US008927834B2

(12) United States Patent
Kidwell et al.

(10) Patent No.: US 8,927,834 B2
(45) Date of Patent: Jan. 6, 2015

(54) GLYPHOSATE-TOLERANT WHEAT GENOTYPES

(71) Applicants: Washington State University, Pullman, WA (US); The United States of America, as represented by the Secretary of Agriculture, Washington, DC (US)

(72) Inventors: Kimberlee Kae Kidwell, Pullman, WA (US); Camille Marie Steber, Pullman, WA (US); Victor Louis Demacon, Pullman, WA (US); Gary Bruce Shelton, Albion, WA (US); Adrienne Bryan Burke, Pullman, WA (US)

(73) Assignees: Washington State University, Pullman, WA (US); The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/134,642

(22) Filed: Dec. 19, 2013

(65) Prior Publication Data
US 2014/0109256 A1 Apr. 17, 2014

Related U.S. Application Data

(63) Continuation of application No. 12/672,504, filed as application No. PCT/US2008/009554 on Aug. 7, 2008, now Pat. No. 8,637,738.

(60) Provisional application No. 60/963,990, filed on Aug. 7, 2007.

(51) Int. Cl.
| | | |
|---|---|---|
| A01H 1/00 | (2006.01) | |
| A01H 5/00 | (2006.01) | |
| C12N 15/01 | (2006.01) | |
| A01H 1/06 | (2006.01) | |
| A01H 5/10 | (2006.01) | |
| A01H 1/02 | (2006.01) | |

(52) U.S. Cl.
CPC ...... *C12N 15/01* (2013.01); *A01H 1/06* (2013.01); *A01H 5/10* (2013.01); *A01H 1/02* (2013.01)
USPC ......... 800/320.3; 800/300; 800/298; 800/266

(58) Field of Classification Search
None
See application file for complete search history.

(56) References Cited

U.S. PATENT DOCUMENTS

| | | | |
|---|---|---|---|
| 6,825,404 B1 * | 11/2004 | Clarkson et al. | 800/320.3 |
| 2004/0064850 A1 * | 4/2004 | Liang et al. | 800/279 |
| 2005/0108798 A1 | 5/2005 | Davis | |
| 2007/0136837 A1 * | 6/2007 | Konzak et al. | 800/278 |

FOREIGN PATENT DOCUMENTS

WO   WO 2005/072186   8/2005

OTHER PUBLICATIONS

Ng et al, Gene polymorphisms in glyphosate-resistant and -susceptible biotypes of Eleusine indica from Malaysia, Weed Res. (2003) 43:108-115.*
Kidwell et al, Registration of "Louise" Wheat, Crop Sci. (2006) 46:1384-1386.*
Kidwell et al., "Registration of 'Louise' Wheat," *Crop Sci.*, vol. 46, pp. 1384-1386, 2006.
Ng et al., "Gene polymorphisms in glyphosate-resistant and -susceptible biotypes of *Eleusine indica* from Malaysia," *Weed Res.*, vol. 43, pp. 108-115, 2003.
Wei et al., "Selection of Glyphosate-Resistant Wheat with Mutation," *Modem Agrichemicals*, vol. 5, No. 3, pp. 42-43, and 46, 2006 (English abstract).
Extended European Search Report with European Search Opinion, dated Oct. 13, 2010.
Supplementary European Search Report, dated Nov. 2, 2010.

\* cited by examiner

*Primary Examiner* — Cathy Kingdon Worley
*Assistant Examiner* — Mykola Kovalenko
(74) *Attorney, Agent, or Firm* — Klarquist Sparkman, LLP

(57) ABSTRACT

The present invention provides methods for producing glyphosate-tolerant wheat genotypes by mutagenesis, glyphosate wheat plants produced by such methods, and related compositions and methods.

14 Claims, No Drawings

GLYPHOSATE-TOLERANT WHEAT GENOTYPES

This is a continuation of U.S. patent application Ser. No. 12/672,504, filed Jan. 31, 2011, which is the U.S. National Stage of International Application No. PCT/US2008/009554, filed Aug. 7, 2008, which was published in English under PCT Article 21(2), which in turn claims the benefit of U.S. Provisional Application No. 60/963,990, filed Aug. 7, 2007, each of which is incorporated herein in their entirety.

BACKGROUND

1. Technical Field

This invention is in the field of wheat (*Triticum aestivum* L.) breeding, specifically relating to wheat genotypes that are tolerant to the herbicide glyphosate.

2. Background Information

Weed competition is a primary cause of yield quality losses in wheat production. Jointed goatgrass, cheat grass and wild oats are major weed problems in wheat production systems in the Pacific Northwest (PNW), and direct seed production is completely reliant on chemical weed control. Most herbicides used to control these weeds are expensive and highly toxic. Yield losses from drought, *Rhizoctonia* root rot and weed competition range from 0% to nearly 100% depending on environmental conditions and the production system used. Developing varieties with resistance or tolerance to any one of these problems will greatly reduce economic risk factors associated with wheat production. Currently *Rhizoctonia* is managed by using glyphosate to eliminate infected plants from the previous year to control the green bridge effect, which typically occurs when fungal pathogens growing on roots of dying weeds and volunteer crops transfer to the roots of emerging cereal crops (Veseth, "'Green Bridge' Key to Root Disease Control," PNW Conservation Tillage Handbook Series No. 16, chap. 4, "Disease Control," pp. 1-8, 1992) The "greenbridge effect" phenomenon often results in significant plant stunting, reduced tillering and grain yield losses (Smiley and Wilkins, Plant Dis. 76:399-404, 1992; Hornby et al., "Take-all and Cereal Production Systems," in: *Take-all Disease of Cereals*, Cambridge, U.K.: CAB International, pp. 103-164, 1998). With the removal of Roundup Ready® wheat (Monsanto Company, St. Louis, Mo.) from the commercialization process due to market acceptability concerns, herbicide-tolerant, transgenic wheat will not be available for many years, if ever.

Weed competition is a primary threat to commercial wheat production, resulting in decreased grain yields and inferior grain quality. Although cultivation can be used to eliminate weeds, soil from tilled fields is highly vulnerable to wind and water erosion. Due to ease of application and effectiveness, herbicide treatment is the preferred method of weed control. Herbicides also permit weed control in reduced tillage or direct seeded cropping systems designed to leave high levels of residue on the soil surface to prevent erosion. The most significant weed competition in wheat comes from highly related grasses, such as wild oat and jointed goatgrass. Unfortunately, it is difficult to devise effective chemical control strategies for problematic weed species related to the cultivated crop since they tend to share herbicide sensitivities. One approach to solving this problem involves the use of recombinant gene transfer to generate crop resistance to broad spectrum herbicides such as glyphosate (i.e. Roundup®) via genetic modification (GM), i.e., through the introduction of foreign gene sequences into plants through recombinant DNA and plant transformation techniques. In this system, herbicide is applied "in-crop" to control weeds without injuring the herbicide-tolerant crop plants. This approach was used to develop Roundup Ready® soybean, cotton, corn and canola varieties, which have been tremendously successful in the U.S. Roundup Ready® soybeans became available for commercial production in 1997, and by 2006, 71 of 75 million acres (95%) of soybeans grown in the U.S. were sown to Roundup Ready® varieties demonstrating the tremendous value of this technology World Wide Web at nass.usda.gov). Producers credit higher net profits, an expanded herbicide application window, enhanced crop safety, and reduced soil erosion due to the elimination of tillage as the primary reasons for the wide-spread acceptance of Roundup Ready® soybeans.

In 1997, the Monsanto Corp. initiated collaborative efforts with private breeding companies and universities across the U.S. to develop Roundup Ready® spring wheat. Since other GM crops were already in commercial production, Roundup Ready® wheat was expected to be readily accepted. However, consumer perception of GM technology in wheat differed dramatically from other crops since wheat is primarily used for human consumption instead of animal feed; therefore, developing GM wheat was highly controversial. Based on economic impact assessments, investigators concluded that commercialization of GM wheat could result in the loss of 30 to 50% of U.S. export markets (Wisner, Economics Staff Report, Iowa State University Dept. of Economics, Ames, Iowa, 2004). Lack of consumer acceptance, particularly in Europe and Asia, eventually led industry representatives, including millers, bakers, and farmer organizations, to ban the production of GM wheat in the U.S. As a result, Monsanto halted the Roundup Ready® wheat development program in May of 2004, eliminating the possibility of using this approach to control problematic weeds in commercial wheat fields.

Alternative methods for developing herbicide-tolerant crop plants are available that do not involve genetic modification per se. Mutation breeding is a non-GM approach involving the use of chemical mutagenesis to increase genetic diversity for traits of agronomic value in crop plants. The process involves exposing seeds to a chemical mutagen, which generates changes in the DNA sequence of the plant resulting in the creation of novel, potentially useful genes that are transmitted from the original mutated plant (M1) to its offspring (M2) through normal sexual reproduction. Useful genes generated through mutation breeding are incorporated into adapted varieties using traditional cross-hybridization techniques. Chemical-induced variants are not considered to be GM since transformation (i.e. genetic engineering) is not used to insert the desired gene into the DNA of the host plant. The herbicide-tolerant Clearfield® Wheat, which is tolerant to Imidazolinone (Immi) herbicides, is the best known example of a wheat variety generated through mutation breeding. See U.S. Pat. No. 6,339,184. The tolerance gene was initially identified in a chemically-induced mutant derived from a French winter wheat variety (Newhouse et al., Plant Physiol. 100:882-886, 1992), and was subsequently transferred into other varieties through traditional breeding. The first Immi-tolerant winter wheat varieties went into commercial production in Colorado in 2003, and Clearfield® varieties are now available in every major winter wheat production region in the U.S. World Wide Web at nass.usda.gov). ORCF101, a Clearfield® variety released by Oregon State University, accounted for 6% of the soft white winter wheat acreage in Washington State in 2006, and acreage of Clearfield® varieties is expected to steadily increase over the next several years. Grain produced from Clearfield® varieties is non-regulated; therefore, it is sold as a bulk commodity without identity preservation or labeling requirements. Mutation breeding has also been used successfully to develop wheat varieties with resistance to powdery mildew (Kinane and Jones, Euphytica 117:251-260, 2001) leaf rust and stem rust (Williams et al., Crop Science 32:612-617, 1992, Friebe et al., Crop Science 34:400-404, 1994, Kerber and Aung, Crop Science 35:743-744, 1995), and yellow and brown rust.

U.S. Pat. No. 7,087,809 describes obtaining glyphosate-tolerant wheat that is tolerant to glyphosate by soaking non-mutagenized wheat seeds in a glyphosate solution and selecting plants that are glyphosate-tolerant.

The well-known "Roundup Ready®" gene used to make glyphosate tolerant soybean and maize by a GM approach is the result of a mutation in a bacterial gene encoding the enzyme target of glyphosate, EPSP synthase (Dill, Pest Manag. Sci. 61:219-224, 2005). Naturally occurring mutations in one or two genes have imparted glyphosate resistance to weed populations in areas where glyphosate was heavily used (Zelaya et al., Theor. Appl. Genet. 110:58-70, 2004; Owen and Zelaya, Pest Manag. Sci. 61:301-311, 2005). In addition, PCR mutagenesis of the cloned rice EPSP synthase gene showed that a single point mutation (C317T, P106L; that is, a single nucleotide change from cytosine to thymidine at nucleotide 317 resulting in an amino acid change in the EPSP protein from proline to lysine at amino acid 106) imparted glyphosate tolerance when transformed into and expressed in resulting transgenic plants (Zhou et al., Plant Physiol. 140: 184-195, 2006). This proline codon is conserved in wheat EPSP synthase. Nonetheless, a majority of scientists in the field has held the opinion that a GM approach for developing glyphosate-tolerant crops was preferable since mutations induced by ethyl methane sulfonate (EMS) resulting in glyphosate-tolerant plants had not been identified to date in any plant species (Jander et al., Plant Physiol. 131:139-146, 2003; Dill, Pest Manag. Sci. 61:219-224, 2005). A screen of 125, 000 mutagenized *Arabidopsis* plants failed to recover a single glyphosate-tolerant plant (Jander et al., Plant Physiol. 131: 139-146, 2003). The authors suggested, "It is likely that no single-base change induced by EMS can produce glyphosate resistance in *Arabidopsis*."

There is a need for new wheat varieties that are glyphosate-tolerant but that do not contain foreign DNA introduced into the plant genome by recombinant DNA techniques. The present invention meets these and other needs.

SUMMARY OF THE INVENTION

We have developed methods for mutagenizing and breeding wheat to produce glyphosate-tolerant wheat genotypes. A number of the wheat genotypes obtained by such methods are tolerant to high levels of glyphosate, in some cases exceeding two, three, or even four times or more of commercial application rates.

According to one aspect of the invention, wheat plants, or parts thereof, are provided that wheat plant, or a part thereof, that are tolerant to an application rate in the field of 3.36 kg/ha or more of the isopropylamine salt of glyphosate, wherein the wheat plants are free from foreign recombinant DNA. That is, no DNA from a non-plant organism or even plant DNA that has been manipulated by recombinant DNA techniques (such as cloning, ligation to another DNA sequence such as a promoter or vector sequence, etc.), has been directly introduced into the wheat plant by transformation or indirectly introduced into the wheat plant by introduction into a wheat plant used in the breeding of the wheat plant. According to another embodiment, such a wheat plant, or said part thereof, comprises a single-gene mutation that confers glyphosate tolerance to 3.36 kg/ha or more of the isopropylamine salt of glyphosate According to another embodiment of the invention, wheat plants, or parts thereof, are provided that comprise a mutation that confers glyphosate tolerance, wherein said mutation is derived from a glyphosate-tolerant wheat genotype selected from the group consisting of: IGT07002-0, IGT07003-No. 1-0, IGT07005-No. 1-0, IGT07006-0, IGT07011-0-0, IGT07013-0-0, IGT07022-0-0, IGT07027-0-0, IGT07028-0-0, IGT07029-0-0, IGT07030-0-0, IGT07031-0-0, IGT07064-0-0, IGT07073-0-0, IGT07074-0-0, IGT07087-0, IGT07091-0, IGT07092-0, EGT07073-0, EGT07081-0, EGT07100-0, EGT07111-0, EGT07118-0, EGT07130-0, EGT07132-0, EGT07138-0, EGT07139-0, EGT07140-0, EGT07143-0, EGT07146-0, EGT07149-0, EGT07154-0, EGT07155-0, EGT07156-0, EGT07158-0, EGT07162-0, EGT07180-0, Re-Mut 3.1 M3 Bulk, Re-Mut 3.2 M3 Bulk, Re-Mut 3.3 M3 Bulk, Re-Mut 3.4 M3 Bulk, Re-Mut 3.5 M3 Bulk, Re-Mut GTL 3.4-10, Macon M2 Bulk FR2 1-10, MaconFR1-16 M4 Bulk, Macon FR3-1 M2, TaraFR1-15-57, TaraFR1-15-94, TaraFR1-20-2, Tara 0.4.1, Tara 0.4.2, Tara 0.4.3, Tara 0.4.4, Tara 0.4.5, Tara 0.4.6, Alpowa M2 Bulk FR2 1-32, Louise M2 Bulk FR2 1-45, Louise Double Mutated M2 Bulk FR2 1-13, Louise FR3-1, Louise FR1-33-6, Louise FR1-42, Louise FR1-43, Louise FR1-62, Louise FR1-65-2, and, Hollis FR1-9-14, and their progeny.

According to another embodiment, such a wheat plant, or part thereof, is tolerant to an application rate in the field of 0.84 kilograms acid equivalent per hectare (kg ae/ha), 1.68 kg ae/ha, 2.52 kg ae/ha, or 3.36 kg ae/ha or more of the isopropylamine salt of glyphosate.

According to another embodiment of such a wheat plant or part thereof, the mutation is a recessive mutation.

More than one mutation can be introduced into a glyphosate-tolerant plant by re-mutagenizing a plant that has a mutation that confers glyphosate tolerance and selecting plants that have the original mutation and a second mutation that confers glyphosate tolerance. Alternatively, in a "gene pyramiding" approach, a second mutation can be introduced into a plant that has a mutation that confers glyphosate tolerance by cross-hybridizing the plant with another plant that has a different mutation (for example, an independent mutation at a second site in its genome, whether in the same or a different gene) that confers glyphosate tolerance, and selecting plants among resulting progeny that have both glyphosate-tolerance mutations. As a further alternative, one of the mutations may be a transgenic trait that is introduced into the wheat plant by recombinant DNA techniques as described in greater detail below.

Therefore, according to another embodiment, such a wheat plant, or part thereof, comprises at least two different mutations that confer glyphosate tolerance, wherein at least one of said at least two different mutations is derived from said glyphosate-tolerant wheat genotype. According to another embodiment of such a wheat plant, or part thereof, each of said at least two different mutations is derived from said glyphosate-tolerant wheat genotype. According to another embodiment of such a wheat plant, or part thereof, said at least two different mutations are mutations of different wheat genes.

According to another embodiment, such a wheat plant, or part thereof, comprises a trait selected from the group consisting of: male sterility, resistance to an herbicide other than glyphosate, insect resistance, disease resistance (including but not limited to resistance to *Rhizoctonia* root rot); waxy starch; modified fatty acid metabolism, modified phytic acid metabolism, modified carbohydrate metabolism, modified waxy starch content, modified gluten content, and modified water stress tolerance.

According to another embodiment, seed of such a wheat plant are provided. According to another embodiment, such seed are true-breeding. According to another embodiment, a wheat plant, or part thereof, is produced by growing such seed.

According to another embodiment, a wheat plant, or part thereof, is provided that has all the physiological and morphological characteristics of a wheat plant of the present invention as described above.

Methods are also provided for producing wheat plants comprising a mutation that confers glyphosate-tolerance and one or more additional desired traits (including glyphosate-tolerance traits and other types of traits) by breeding. Therefore, according to another embodiment of the invention, methods are provided of producing a glyphosate-tolerant plant comprising: (a) crossing a plant of a selected wheat variety with a glyphosate-tolerant wheat plant as described above, thereby producing a plurality of progeny; (b) selecting a progeny that is glyphosate-tolerant. According to one such embodiment, the method comprises: (a) crossing plants grown from seed of said glyphosate-tolerant wheat plant according to the present invention as described above with plants of said selected wheat variety to produce $F_1$ progeny plants; (b) selecting $F_1$ progeny plants that have the glyphosate-tolerance trait; (c) crossing the selected $F_1$ progeny plants with the plants of said selected wheat variety to produce backcross progeny plants; (d) selecting for backcross progeny plants that have the glyphosate-tolerance trait and physiological and morphological characteristics of said selected wheat genotype to produce selected backcross progeny plants; and (e) repeating steps (c) and (d) three or more times in succession to produce selected fourth or higher backcross progeny plants that comprise the glyphosate tolerance trait and all of the physiological and morphological characteristics of said selected wheat genotype as determined at the 5% significance level when grown in the same environmental conditions. According to another embodiment of the invention, methods are provided of producing a glyphosate-tolerant plant that comprise: (a) crossing plants grown from seed of said glyphosate-tolerant wheat plant of claim 3 with plants of said selected wheat variety to produce $F_1$ progeny plants, wherein the selected wheat variety comprises a desired trait; (b) selecting $F_1$ progeny plants that have the desired trait to produce selected $F_1$ progeny plants; (c) crossing the selected progeny plants with the plants of said glyphosate-tolerant wheat genotype to produce backcross progeny plants; (d) selecting for backcross progeny plants that have the desired trait and physiological and morphological characteristics of said glyphosate-tolerant wheat genotype to produce selected backcross progeny plants; and (e) repeating steps (c) and (d) three or more times in succession to produce selected fourth or higher backcross progeny plants that comprise the desired trait and all of the physiological and morphological characteristics of said glyphosate-tolerant wheat genotype as determined at the 5% significance level when grown in the same environmental conditions. According to another such embodiment, the desired trait is selected from the group consisting of male sterility, herbicide resistance, insect resistance, disease resistance (including but not limited to resistance to *Rhizoctonia* root rot) and waxy starch.

It will be apparent to the skilled artisan that the methods of the present invention may be applied to obtain glyphosate-tolerant mutants of other grass species, such as cereal grain crops including but not limited to triticale, rye, barley, millet, maize, rice, sorghum, and so on.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

According to one embodiment of the invention, glyphosate-tolerant wheat varieties are provided. The term "glyphosate tolerant" (or, alternatively, "glyphosate resistant") is used herein to mean that the plant, or part thereof (such as a seed), detectably differs from a control plant in its ability to resist the effects of glyphosate herbicide, including, but not limited to, improved survival, higher growth rate, higher yield, etc.

There are many analytical methods available to determine the homozygotic stability, phenotypic stability, and identity of wheat varieties. For a particular trait such as, for example, glyphosate tolerance, to be of commercial value, it must be heritable and exhibit stable expression.

The oldest and most traditional method of analysis is the observation of phenotypic traits. The data is usually collected in field experiments over the life of the wheat plants to be examined. Phenotypic characteristics most often observed are for traits such as seed yield, head configuration, glume configuration, seed configuration, lodging resistance, disease resistance, maturity, etc.

In addition to phenotypic observations, the genotype of a plant also can be examined through segregation analysis or the use of biotechnology. There are many laboratory-based techniques available for the analysis, comparison and characterization of plant genotype; among these are gel electrophoresis, isozyme electrophoresis, restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) which also are referred to as microsatellites, and single nucleotide polymorphisms (SNPs). Gel electrophoresis is particularly useful in wheat. Wheat variety identification is possible through electrophoresis of gliadin, glutenin, albumin and globulin, and total protein extracts (Bietz, pp. 216-228, "Genetic and Biochemical Studies of Nonenzymatic Endosperm Proteins" *In Wheat and Wheat Improvement*, ed. E. G. Heyne, 1987).

Description of Wheat Variety Louise. Wheat genotype GT Louise was obtained by selection of glyphosate-tolerant plants derived from the wheat variety Louise as described in Example 1. Further backcrosses using conventional methods are performed in order to produce a true-breeding glyphosate-tolerant wheat variety derived from wheat genotype GT Louise.

'Louise' soft white spring wheat (*Triticum aestivum* L.) (PI 634865) was developed and released in August 2005 as a replacement for the soft white spring variety 'Zak' (Kidwell et al., Crop Sci. 42:661-662, 2002) in the intermediate to high rainfall (>400 mm of average annual precipitation), non-irrigated wheat production regions of Washington State based on its superior end-use quality, high grain yield potential, high-temperature adult-plant resistance to local races of stripe rust (caused by *Puccinia striiformis* Westend. f. sp. *tritici*), and partial resistance to the Hessian fly [*Mayetiola destructor* (Say)].

Louise is an $F_{4:5}$ head row selection derived from the cross 'Wakanz' (PI 506352)/'Wawawai' (PI 574538), which was made in 1992. The following modified pedigree-bulk breeding method was used to advance early generation progeny. Bulked seed (30 g) from $F_1$ plants was used to establish an $F_2$ field plot. Approximately 100 heads were selected at random from individual $F_2$ plants, and a 40 g sub-sample of the bulked seed was used to establish a single $F_3$ plot. Seed from the $F_3$ plot was bulk harvested, and a 60-g sub-sample was used to establish an $F_4$ field plot. Single heads from approximately 150 $F_4$ plants were threshed individually to establish $F_{4:5}$ head row families. Following selection among rows for general adaptation, plant height and grain appearance, seed from 30 to 50 plants within each selected head row was bulk harvested to obtain $F_{4:6}$ seed for grain yield assessment trials. The $F_1$, $F_2$, $F_4$ and $F_5$ progeny were advanced in field nurseries at Pullman, Wash., whereas $F_3$ progeny were advanced at the Lind Dryland Experiment Station in Lind, Wash. Breeder seed of Louise was produced as a reselection, based on phenotypic uniformity, of 1100 $F_{4:11}$ head rows grown under irrigation in Othello, Wash. in 2003. Selected head rows were bulked at harvest, resulting in the production of 563 kg of breeder seed.

Louise is an intermediate height, semi-dwarf cultivar. It has lax, tapering, inclined curved heads with white awns and white glumes that are long in length, wide in width with medium, apiculate shoulders, and narrow beaks. Louise has elliptical kernels that are white, soft and smooth. Seed of Louise has a mid-sized germ with a narrow, mid-depth crease, angular cheeks and a medium, non-collared brush.

In greenhouse seedling tests conducted in 2003 and 2004 under a low diurnal temperature cycle gradually changing from 4° C. at 2:00 am to 20° C. at 2:00 pm (Chen and Line, Phytopathology 82:1428-1434, 1992) reaction to wheat stripe rust races PST-37, PST-43, PST-45, PST-78 and PST-98 was assessed. Louise was susceptible to all races indicating that it does not have all-stage (seedling) resistance. However, when tested with races PST-78 and PST-100 in adult-plant stages under a high diurnal temperature cycle gradually changing from 10° C. at 2:00 am to 35° C. at 2:00 pm, Louise was highly resistant indicating that it has high-temperature, adult-plant (HTAP) resistance (Chen and Line, Phytopathology 85:567-572, 1995). In field tests conducted in various locations in Washington State from 2001 to 2004, Louise displayed a high level of non-race-specific, HTAP resistance to the primary virulent races of current stripe rust populations in the Pacific Northwest region of the United States, including PST-78, PST-98 and PST-100. On the basis of insect screening trials conducted at the University of Idaho using a collection containing the three primary biotypes found in the PNW, Louise is heterogeneous (65%) for resistance to Hessian fly biotypes E, F and GP. On the basis of pedigree and natural field infestation ratings from Pullman, Wash., Louise is susceptible to the Russian wheat aphid [*Diuraphis noxia* (Mordvilko)].

Louise was evaluated in replicated field trials under fallow, non-irrigated and irrigated conditions. Grain yields of Louise typically equaled or exceeded those of soft white spring entries in nonirrigated and irrigated field evaluations conducted in Washington, Oreg., and Idaho from 2002 to 2004. In 51 tests conducted across 3 yr in Washington State, the average grain yield of Louise was 3702 kg ha$^{-1}$, which was significantly (P<0.05) higher than the yield averages of Zak (3232 kg ha$^{-1}$) and Alturas (3581 kg ha$^{-1}$) (Souza et al., Crop Sci. 44:1477-1478, 2004) and comparable to Alpowa (3668 kg ha$^{-1}$), (PI 566596) and Nick (3742 kg ha$^{-1}$) (proprietary cultivar from WestBred LLC). On the basis of 24 site-years of data from the intermediate and high rainfall zones (>400 mm average annual precipitation), the average grain yield of Louise (4952 kg ha$^{-1}$) was equivalent to Alpowa (4905 kg ha$^{-1}$) and Nick (4831 kg ha$^{-1}$), and significantly (P<0.05) higher than Alturas (4690 kg ha$^{-1}$) and Zak (4280 kg ha$^{-1}$).

On the basis of 51 tests, grain volume weight of Louise averaged 757 kg m$^{-3}$, which was significantly higher (P<0.05) than that of Zak (750 kg m$^{-3}$), similar to Alturas (756 kg m$^{-3}$) and Nick (763 kg m$^{-3}$), and significantly (P<0.05) lower than Alpowa (771 kg m$^{-3}$). Thousand-kernel weight averages of Louise, Zak, Alpowa, Alturas, and Nick were 50.1, 44.5, 44.7, 34.7, and 36.4 g, respectively. The average plant height of Louise was 80 cm, which was 4 cm, 6 cm, 8 cm and 9 cm taller than Zak (76 cm), Alpowa (74 cm), Nick (72 cm) and Alturas (71 cm), respectively. Lodging percentages of Louise (5 to 10%) when grown with irrigation were comparable to Alpowa (5 to 10%), higher than Nick (2 to 5%) and Alturas (2 to 5%), and lower than Zak (25 to 30%). Louise headed 1 d earlier than Zak [Day of Year (DOY) 168], on the same date as Alpowa (DOY 167), one d later than Alturas (DOY 166), and 2 d later than Nick (DOY 165).

In tests conducted at the USDA-ARS Western Wheat Quality Laboratory in Pullman, Wash. using grain produced in breeding and commercial variety testing trials in Washington State from 2002 through 2004, grain protein content of Louise (117 g kg$^{-1}$) was similar to Alpowa and Alturas (116 g kg$^{-1}$), and lower than Nick (120 g kg$^{-1}$) and Zak (123 g kg$^{-1}$). Flour yield of Louise (671 g kg$^{-1}$) was comparable to Zak (667 g kg$^{-1}$), Alturas (666 g kg$^{-1}$) and Nick (665 g kg$^{-1}$), and significantly (P<0.01) higher than Alpowa (640 g kg$^{-1}$). Flour ash content for Louise (3.6 g kg$^{-1}$) was similar to Alpowa (3.5 g kg$^{-1}$) and significantly (P<0.01) lower than Zak (3.9 g kg$^{-1}$), Alturas (3.7 g kg$^{-1}$) and Nick (3.8 g kg$^{-1}$). Louise had a higher average milling score (84.0) than Zak (81.4), Alpowa (80.6), Alturas (82.4), and Nick (81.5). Mixograph water absorption of Louise was identical to Zak and Nick (531 g kg$^{-1}$), slightly lower than Alpowa (534 g kg$^{-1}$), and significantly (P<0.01) lower than Alturas (544 g kg$^{-1}$). Average cookie diameter for Louise (9.7 cm) was comparable to Zak (9.7 cm) and larger than Alpowa (9.3 cm), Alturas (9.5 cm), and Nick (9.5 cm), and average sponge cake volume of Louise (1305 cm$^3$) was smaller than Zak (1322 cm$^3$) and Alpowa (1362 cm$^3$) and larger than Alturas (1225 cm$^3$) and Nick (1230 cm$^3$) when compared across production regions.

Foundation seed of Louise is maintained by the Washington State Crop Improvement Association under supervision of the Department of Crop and Soil Sciences and the Washington State Agricultural Research Center and seed has been deposited with the National Plant Germplasm System.

Area of Adaptability. When referring to area of adaptability, such term is used to describe the location with the environmental conditions that would be well suited for this wheat genotype. Area of adaptability is based on a number of factors, for example: days to heading, winter hardiness, insect resistance, disease resistance, and drought resistance. Area of adaptability does not indicate that the wheat genotype will grow in every location within the area of adaptability or that it will not grow outside the area. For example, areas of adaptability in the U.S. (using the standard two-letter code for states) include: (a) Northern area, including the states of DE, IL, IN, MI, MO, NJ, NY, OH, PA, WI and Ontario, Canada; (b) Mid-south, including the states of AR, KY, MO boot heel and TN; (c) Southeast, including the states of NC, SC, and VA; and (d) Deep South, including the states of AL, GA, LA, and MS. Nonetheless, wheat genotypes according to the present invention may be grown within and outside areas of adaptability, whether in the United States or outside the United States.

Wheat Breeding. Field crops are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The term cross-pollination herein does not include self-pollination or sib-pollination. Wheat plants (Triticum aestivum L.), are recognized to be naturally self-pollinated plants which, while capable of undergoing cross-pollination, rarely do so in nature (the natural outcrossing level in wheat is about 5%). Thus intervention for control of pollination is critical to the establishment of superior varieties.

A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny. The term "homozygous plant" is hereby defined as a plant with homozygous genes at 95% or more of its loci. The term "inbred" or "true breeding" as used herein refers to a homozygous plant or a collection of homozygous plants.

Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. In general breeding starts with cross-hybridizing of two genotypes (a "breeding cross"), each of which may have one or more desirable characteristics that is lacking in the other or which complements the other. If the two original parents do not provide all the desired characteristics, other sources can be included by making more crosses. In each successive filial generation, $F_1 \rightarrow F_2$; $F_2 \rightarrow F_3$; $F_3 \rightarrow F_4$; $F_4 \rightarrow F_5$, etc., plants are selfed to increase the homozygosity of the line. Typically in a breeding program five or more generations of selection and selfing are practiced to obtain a homozygous plant.

Pedigree breeding is commonly used for the improvement of self-pollinating crops. Two parents that possess favorable, complementary traits are crossed to produce an $F_1$. An $F_2$ population is produced by selfing or sibbing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_5$, $F_6$ and $F_7$), the best lines or mixtures of phenotypically similar lines are tested for potential release as new varieties.

Backcross breeding has been used to transfer genes for simply inherited, qualitative, traits from a donor parent into a desirable homozygous variety that is utilized as the recurrent parent. The source of the traits to be transferred is called the donor parent.

After the initial cross, individuals possessing the desired trait or traits of the donor parent are selected and then repeatedly crossed (backcrossed) to the recurrent parent. The resulting plant is expected to have the attributes of the recurrent parent (e.g., variety) plus the desirable trait or traits transferred from the donor parent. This approach has been used extensively for breeding disease resistant varieties.

Each wheat breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination and the number of hybrid offspring recovered from each successful cross. Recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Plants from the populations can be selected and self-pollinated to create new varieties.

Another breeding method is single-seed descent. This procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed. In a multiple-seed procedure, wheat breeders commonly harvest one or more spikes (heads) from each plant in a population and thresh them together to form a bulk. Part of the bulk is used to plant the next generation and part is put in reserve. The procedure has been referred to as modified single-seed descent. The multiple-seed procedure has been used to save labor at harvest. It is considerably faster to thresh spikes with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Bulk breeding also can be used. In the bulk breeding method an $F_2$ population is grown. The seed from the populations is harvested in bulk and a sample of the seed is used for planting the next season. This cycle can be repeated several times. In general when individual plants are expected to have a high degree of homozygosity, individual plants are selected, tested, and increased for possible use as a variety.

Molecular markers including techniques such as starch gel electrophoresis, isozyme eletrophoresis, restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs), and single nucleotide polymorphisms (SNPs) may be used in plant breeding methods. One use of molecular markers is quantitative trait loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers also can be used during the breeding process for the selection of qualitative and quantitative traits. For example, markers closely linked to alleles or markers containing sequences within the actual alleles of interest can be used to select plants that contain the alleles of interest during a backcrossing breeding program. The markers also can be used to select for the genome of the recurrent parent and against the markers of the donor parent. Using this procedure can minimize the amount of genome from the donor parent that remains in the selected plants. It also can be used to reduce the number of crosses back to the recurrent parent needed in a backcrossing program (Openshaw et al. Marker-assisted Selection in Backcross Breeding. In: Proceedings Symposium of the Analysis of Molecular Marker Data, 5-6 Aug. 1994, pp. 41-43. Crop Science Society of America, Corvallis, Oreg.). The use of molecular markers in the selection process is often called Genetic Marker Enhanced Selection or Marker-Assisted Selection.

The production of double haploids also can be used for the development of homozygous lines in the breeding program. Double haploids are produced by the doubling of a set of chromosomes (1N) from a heterozygous plant to produce a completely homozygous individual. This can be advantageous because the process omits the generations of selfing needed to obtain a homogygous plant from a heterozygous source. Various methodologies of making double haploid plants in wheat have been developed (Laurie, D. A. and S. Reymondie, *Plant Breeding*, 1991, v. 106:182-189. Singh, N. et al., *Cereal Research Communications*, 2001, v. 29:289-296; Redha, A. et al., *Plant Cell Tissue and Organ Culture*, 2000, v. 63:167-172; U.S. Pat. No. 6,362,393)

Though pure-line varieties are the predominate form of wheat grown for commercial wheat production hybrid wheat also is used. Hybrid wheat plants are produced with the help of cytoplasmic male sterility, nuclear genetic male sterility, or chemicals. Various combinations of these three male sterility systems have been used in the production of hybrid wheat.

Descriptions of other breeding methods that are commonly used for different traits and crops can be found in one of several reference books (e.g., Allard, *Principles of Plant Breeding*, 1960; Simmonds, *Principles of Crop Improvement*, 1979; editor Heyne, *Wheat and Wheat Improvement*, 1987; Allan, "Wheat", Chapter 18, *Principles of Crop Development*, vol. 2, Fehr editor, 1987).

Promising advanced breeding lines are thoroughly tested and compared to appropriate standards in environments representative of the commercial target area(s). The best lines are candidates for new commercial varieties; those still deficient in a few traits may be used as parents to produce new populations for further selection.

A most difficult task is the identification of individuals that are genetically superior, because for most traits the true genotypic value is masked by other confounding plant traits or environmental factors. One method of identifying a superior genotype is to observe its performance relative to other experimental genotypes and to a widely grown standard variety. Generally a single observation is inconclusive, so replicated observations are required to provide a better estimate of its genetic worth.

A breeder uses various methods to help determine which plants should be selected from the segregating populations and ultimately which lines will be used for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which lines, are significantly better or different for one or more traits of interest. Experimental design methods are used to control error so that differences between two lines can be more accurately determined. Statistical analysis includes the calculation of mean values, determination of the statistical significance of the sources of variation, and the calculation of the appropriate variance components. Five and one percent significance levels are customarily used to determine whether a difference that occurs for a given trait is real or due to the environment or experimental error.

Plant breeding is the genetic manipulation of plants. The goal of wheat breeding is to develop new, unique and superior wheat varieties. In practical application of a wheat breeding program, the breeder initially selects and crosses two or more parental lines, followed by repeated selfing and selection, producing many new genetic combinations. The breeder can theoretically generate billions of different genetic combinations via crossing, selfing and naturally induced mutations. The breeder has no direct control at the cellular level. Therefore, two breeders will never develop exactly the same line.

Each year, the plant breeder selects the germplasm to advance to the next generation. This germplasm is grown under unique and different geographical, climatic and soil conditions, and further selections are then made during and at the end of the growing season.

Proper testing should detect major faults and establish the level of superiority or improvement over current varieties. In addition to showing superior performance, there must be a demand for a new variety. The new variety must be compatible with industry standards, or must create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. It must also be feasible to produce seed easily and economically.

These processes, which lead to the final step of marketing and distribution, can take from six to twelve years from the time the first cross is made. Therefore, development of new varieties is a time-consuming process that requires precise forward planning, efficient use of resources, and a minimum of changes in focused direction.

Wheat (*Triticum aestivum* L.), is an important and valuable field crop. Thus, a continuing goal of wheat breeders is to develop stable, high yielding wheat varieties that are agronomically sound and have good milling and baking qualities for its intended use. To accomplish this goal, the wheat breeder must select and develop wheat plants that have the traits that result in superior varieties.

Any known trait can be introduced into a wheat variety by breeding using a donor plant that has the desired trait. One example of such a desirable trait is resistance to *Rhizoctonia* root rot. Co-pending U.S. provisional patent application Ser. No. 60/771,402, which is incorporated herein by reference, describes the development of wheat plants that have resistance to *Rhizoctonia* root rot by mutation breeding and that would be useful for the breeding of wheat that has both glyphosate-tolerance and resistance to *Rhizoctonia* root rot.

Glyphosate Formulations and Spray Tests. In one embodiment a greenhouse or field evaluation for glyphosate tolerance is conducted. The term "glyphosate" is used herein to refer collectively to the parent herbicide N-phosphonomethylglycine (otherwise known as glyphosate acid), to a salt or ester thereof, or to a compound which is converted to N-phosphonomethylglycine in plant tissues or which otherwise provides N-phosphonomethylglycine in ionic form (otherwise known as glyphosate ion). Illustratively, water-soluble glyphosate salts useful herein are disclosed in U.S. Pat. Nos. 3,799,758 and 4,405,531 to Franz, the disclosure of which is incorporated herein by reference. Glyphosate salts that can be used according to the present invention include but are not restricted to alkali metal, for example sodium and potassium, salts; ammonium salt; $C_{1-16}$ alkylammonium, for example dimethylammonium and isopropylammonium, salts; $C_{1-16}$ alkanolammonium, for example monoethanolammonium, salt; $C_{1-16}$ alkylsulfonium, for example trimethylsulfonium, salts; mixtures thereof and the like. The glyphosate acid molecule has three acid sites having different pKa values; accordingly mono-, di- and tribasic salts, or any mixture thereof, or salts of any intermediate level of neutralization, can be used.

Glyphosate salts are commercially significant in part because they are water-soluble. Many ammonium, alkylammonium, alkanolammonium, alkylsulfonium and alkali metal salts are highly water-soluble, allowing for formulation as highly concentrated aqueous solutions which can be diluted in water at the point of use.

Such concentrated aqueous solutions can contain about 50 to about 500 grams per liter of glyphosate, expressed as acid equivalent (g a.e./l). Higher glyphosate concentrations, for example about 300 to about 500 g a,e,/l, also may be used.

Selecting the proper rate for the situation and using the appropriate additives are the key considerations in obtaining consistent control with glyphosate products. Several different concentrations of glyphosate are now being marketed, so it is important to adjust rates according to the product used. Glyphosate labels usually state the concentration in two ways: (a) lbs per gal of formulated glyphosate and (b) lbs per gal of acid equivalent of glyphosate. For example, Roundup Ultra® contains 4 lbs per gal of the isopropylamine salt of glyphosate but only 3 lbs per gal acid equivalent of glyphosate. The first value includes the weight of the salt formulated with glyphosate, whereas the second only measures how much glyphosate is present. Since the salt does not contribute to weed control, the acid equivalent is a more accurate method of expressing concentrations and weed killing ability.

Glyphosate salts are alternatively formulated as water-soluble or water-dispersible compositions, in the form for example of powders, granules, pellets or tablets. Such compositions are often known as dry formulations, although the term "dry" should not be understood in this context to imply the complete absence of water. Typically, dry formulations contain less than about 5% by weight of water, for example about 0.5% to about 2% by weight of water. Such formulations are intended for dissolution or dispersion in water at the point of use.

Contemplated dry glyphosate formulations can contain about 5% to about 80% by weight of glyphosate, expressed as acid equivalent (% a.e.). Higher glyphosate concentrations within the above range, for example about 50% to about 80% a.e., are preferred. Especially useful salts of glyphosate for making dry formulations are sodium and ammonium salts.

Plant treatment compositions and liquid and dry concentrate compositions of the invention can optionally contain one or more desired excipient ingredients. Especially useful excipient ingredients for glyphosate compositions are surfactants, which assist in retention of aqueous spray solutions on the relatively hydrophobic surfaces of plant leaves, as well as helping the glyphosate to penetrate the waxy outer layer (cuticle) of the leaf and thereby contact living tissues within the leaf. Surfactants can perform other useful functions as well.

There is no restriction in the type or chemical class of surfactant that can be used in glyphosate compositions of the invention. Nonionic, anionic, cationic and amphoteric types, or combinations of more than one of these types, are all useful in particular situations. However, it is generally the case that at least one of the surfactants, if any, present should be other than anionic; i.e., at least one of the surfactants should be nonionic, cationic or amphoteric.

Standard reference sources from which one of skill in the art can select suitable surfactants, without limitation to the above mentioned classes, include Handbook of Industrial Surfactants, Second Edition (1997) published by Gower, McCutcheon's Emulsifiers and Detergents, North American and International Editions (1997) published by MC Publishing Company, and International Cosmetic Ingredient Dictionary, Sixth Edition (1995) Volumes 1 and 2, published by the Cosmetic, Toiletry and Fragrance Association.

Other optional components of compositions of the invention include agents to modify color, viscosity, gelling properties, freezing point, hygroscopicity, caking behavior, dissolution rate, dispersibility, or other formulation characteristics.

Examples of commercial formulations of glyphosate include, without restriction, those sold by Monsanto Company as Roundup®, Roundup Ultra®, Roundup CT®, Roundup Extra®, Roundup Biactive®, Roundup Bioforce®, Rodeo®, Polaris®, Spark® and Accord® herbicides, all of which contain glyphosate as its isopropylammonium salt; those sold by Monsanto Company as Roundup Dry® and Rival® herbicides, which contain glyphosate as its ammonium salt; that sold by Monsanto Company as Roundup Geoforce®, which contains glyphosate as its sodium salt; and that sold by Zeneca Limited as Touchdown® herbicide, which contains glyphosate as its trimethylsulfonium salt.

The selection of application rates for a glyphosate formulation that are biologically effective is within the skill of the ordinary agricultural technician. One of skill in the art will likewise recognize that individual plant conditions, weather conditions and growing conditions can affect the results achieved in practicing the process of the present invention.

Over two decades of glyphosate use and published studies relating to such use have provided abundant information from which a weed control practitioner can select glyphosate application rates that are herbicidally effective on particular species at particular growth stages in particular environmental conditions.

In one embodiment, a glyphosate-containing herbicide is applied to the plant comprising a glyphosate-tolerance trait according to the present invention, and the plants are evaluated for tolerance to the glyphosate herbicide. Any formulation of glyphosate can be used for testing plants. For example, a glyphosate composition such as Roundup Ultra® can be used. The testing parameters for an evaluation of the glyphosate tolerance of the plant will vary depending on a number of factors. Factors would include, but are not limited to the type of glyphosate formulation, the concentration and amount of glyphosate used in the formulation, the type of plant, plant developmental stage during the time of the application, environmental conditions, the application method, and the number of times a particular formulation is applied. For example, plants can be tested in a greenhouse environment using a spray application method. The testing range using Roundup Ultra® can include, but is not limited to 8 oz/acre to 256 oz/acre. The preferred commercially effective range can be from 16 oz/acre to 64 oz/acre of Roundup Ultra®, depending on the crop and stage of plant development. A crop can be sprayed with at least one application of a glyphosate formulation. For testing in wheat an application of 32 oz/acre of Roundup Ultra® at the 3 to 5 leaf stage can be used and may be followed with a pre- or post-harvest application, depending on the type of wheat to be tested. The test parameters can be optimized for each crop in order to find the particular plant comprising the constructs of the present invention that confers the desired commercially effective glyphosate tolerance level.

For reference purposes, the commercial application rate is 32 oz/A of Roundup Ultra®, which is equivalent to 0.84 kg ae/ha or 0.75 lbs. ae/A. A discussion of various formulations of glyphosate, their glyphosate concentrations and equivalent application rates is provided, for example, in "Sorting Through the Glyphosate Jungle" by Alan York of North Carolina State University, available on the World Wide Web at ces.ncsu.edu/martin/glyphosate.html. p Tissue Culture and Regeneration. Further reproduction of the glyphosate-tolerant wheat genotypes of the invention can occur by tissue culture and regeneration. Tissue culture of various tissues of wheat and regeneration of plants therefrom is well known and widely published. A review of various wheat tissue culture protocols can be found in "In Vitro Culture of Wheat and Genetic Transformation-Retrospect and Prospect" by Maheshwari et al. (*Critical Reviews in Plant Sciences,* 14(2): pp 149-178, 1995). Thus, another aspect of this invention is to provide cells which upon growth and differentiation produce wheat plants capable of having the physiological and morphological characteristics of the glyphosate-tolerant wheat genotypes of the invention.

Plant Parts. As used herein, the term "plant parts" includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like. The term also includes products of a plant, including but not limited to flour, starch, oil, wheat germ, and so on.

Isolated Glyphosate-Tolerance Gene Sequences and their Use. Also, contemplated by the instant invention are the nucleic acids which comprise the genes, which when expressed in the wheat plant provide herbicide resistance in wheat plants. Any DNA sequences, whether from a different species or from the same species, which are inserted into the genome using transformation are referred to herein collectively as "transgenes".

The genetic sequences that comprise mutations responsible for conferring glyphosate tolerance to the wheat plants of the present invention can be genetically mapped, identified, isolated, and the sequence determined by those of ordinary skill in the art. See, for example: Plant Genomes: Methods for Genetic and Physical Mapping, J. S. Beckmann and T. C. Osborn, 1992, Kluwer Academic Publishers; Genome Mapping in Plants, Paterson, 1996, Harcourt Brace and Co.; Wheat Genome Mapping, A. Kalinski, 1996, Diane Publishing Co.; and Methods in Molecular Biology, Vol. 82, *Arabidopsis* Protocols, Martinez Zapater and Salinas, 1998, Humana Press. The isolated nucleic acid encoding the gene conferring the naturally-occurring herbicide resistance encodes a protein responsible for causing the plant to be herbicide tolerant. This isolated nucleic acid can then be used to: (1) identify other nucleic acids which may contain naturally-occurring mutations that provide herbicide resistance to wheat plants; (2) introduce the isolated nucleic acid into a wheat plant which lacks herbicide resistance by means of genetic engineering; (3) insert the isolated nucleic acid into a suitable vector which can be expressed in a wheat plant; and (4) insert the vector into a plant cell (e.g., a wheat plant cell).

The present invention also contemplates the fabrication of DNA constructs comprising the isolated nucleic acid sequence containing the coding sequence from the gene that confers herbicide resistance operatively linked to plant gene expression control sequences. "DNA constructs" are defined herein to be constructed (not naturally-occurring) DNA molecules useful for introducing DNA into host cells, and the term includes chimeric genes, expression cassettes, and vectors.

As used herein "operatively linked" refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis et al., Molecular Cloning: A Laboratory Manual, Cold Spring Harbor, N.Y., 1982; and Sambrook et al., Molecular Cloning: A Laboratory Manual, Cold Spring Harbor, N.Y., 1989.

"Expression control sequences" are DNA sequences involved in any way in the control of transcription or translation. Suitable expression control sequences and methods of making and using them are well known in the art.

The expression control sequences include a promoter. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-2361, 1987. Also, the location of the promoter relative to the transcription start may be optimized. See, e.g., Roberts et al., Proc. Natl. Acad. Sci. USA, 76:760-764, 1979. Many suitable promoters for use in plants are well known in the art.

For instance, suitable constitutive promoters for use in plants include the promoters of plant viruses, such as the peanut chlorotic streak caulimovirus (PC 1 SV) promoter (U.S. Pat. No. 5,850,019); the 35S and 19S promoter from cauliflower mosaic virus (CaMV) (Odell et al., 1313:3810-812, 1985); promoters of the *Chlorella* virus methyltransferase genes (U.S. Pat. No. 5,563,328); the full-length transcript promoter from figwort mosaic virus (FMV) (U.S. Pat. No. 5,378,619); the promoters from such genes as rice actin (McElroy et al., Plant Cell 2:163-171, 1990), ubiquitin (Christiansen et al., Plant Mol. Biol. 12:619-632, 1989), and (Christiansen et al., Plant Mol. Biol. 18: 675-689, 1992), pEMU (Last et al., Theor. Appl. Genet. 81:581-588, 1991), MAS (Velten et al., Embo J. 3:2723-2730, 1984), wheat histone (Lepetit et al., Mol. Gen. Genet. 231:276-285, 1992), and Atanassova et al., Plant Journal 2:291-300, 1992), *Brassica napus* ALS3 (International Publication No. WO 97/41228); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al., Proc. Natl. Acad. Sci. 90:4567-4571, 1993): the promoter of the wheat In 2 gene which responds to benzenesulfonomide herbicide safeners (U.S. Pat. No. 5,364,780 and Gatz et al., Mol. Gen. Genet. 243:32-38, 1994), and the promoter of the Tet repressor from Tn10 (Gatz et al., Mol. Gen. Genet. 227:229-237, 1991). According to one embodiment, the promoter for use in plants is one that responds to an inducing agent to which plants normally do not respond. An exemplary inducible promoter of this type is the inducible promoter from a steroid hormone gene, the transcriptional activity of which is induced by a glucosteroid hormone (Schena et al., Proc. Natl. Acad. Sci. 88:10421, 1991) or the application of a chimeric transcription activator, XVE, for use in an estrogen receptor-based inducible plant expression system activated by estradiol (Zou et al., Plant J. 24 265-273, 2000). Other inducible promoters for use in plants are described in European Patent No. 332104, International Publication No. WO 93/21334 and International Publication No. WO 97/06269, and discussed in Gatz and Lenk Trends Plant Sci., 3:352-358, 1998, and Zou and Chua, Curr. Opin. Biotechnol., 11:146-151, 2000.

Finally, promoters composed of portions of other promoters and partially or totally synthetic promoters can be used. See, e.g., Ni et al., Plant J. 7:661-676, 1995, and International Publication No. WO 95/14098, which describe such promoters for use in plants.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PC1SV enhancer element (U.S. Pat. No. 5,850,019), the CaMV 35S enhancer element (U.S. Pat. Nos. 5,106,739 and 5,164,316), and the FMV enhancer element (Maiti et al., Transgenic Res., 6:143-156, 1997). See also, International Publication No. WO 96/23898 and Enhancers and Eukaryotic Expression (Cold Spring Harbor Press, Cold Spring Harbor, N.Y., 1983).

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants and other eukaryotes. Suitable 3' untranslated sequences for use in plants include those of the cauliflower mosaic virus 35S gene, the phaseolin seed storage protein gene, the pea ribulose-1, 5-bisphosphate carboxylase small subunit E9 gene, the wheat 7S storage protein gene, the octopine synthase gene, and the nopaline synthase gene.

A 5' untranslated leader sequence also can be employed. The 5' untranslated leader sequence is the portion of an mRNA which extends from the 5' CAP site to the translation initiation codon. This region of the mRNA is necessary for translation initiation in plants and plays a role in the regulation of gene expression. Suitable 5' untranslated leader sequence for use in plants includes those of alfalfa mosaic virus, cucumber mosaic virus coat protein gene, and tobacco mosaic virus.

The DNA construct may be a vector. The vector may contain one or more replication systems which allow it to replicate in host cells. Self-replicating vectors include plasmids, cosmids and virus vectors. Alternatively, the vector may be an integrating vector which allows the integration into the host cell's chromosome of the DNA sequence encoding the herbicide resistance gene product. The vector desirably also has unique restriction sites for the insertion of DNA sequences. If a vector does not have unique restriction sites it may be modified to introduce or eliminate restriction sites to make it more suitable for further manipulation.

Vectors suitable for use in expressing the nucleic acids, which when expressed in a plant confer herbicide resistance, include but are not limited to pMON979, pMON977, pMON886, pCaMVCN, and vectors derived from the tumor inducing (Ti) plasmid of *Agrobacterium tumefaciens* described by Rogers et al., Meth. Enzymol., 153:253-277, 1987. The nucleic acid is inserted into the vector such that it is operably linked to a suitable plant active promoter. Suitable plant active promoters for use with the nucleic acids include, but are not limited to CaMV35S, ACTJN, FMV35S, NOS and PCSLV promoters. The vectors comprising the nucleic acid can be inserted into a plant cell using a variety of known methods. For example, DNA transformation of plant cells include but are not limited to *Agrobacterium*-mediated plant transformation, protoplast transformation, electroporation, gene transfer into pollen, injection into reproductive organs, injection into immature embryos and particle bombardment. These methods are described more fully in U.S. Pat. No. 5,756,290, and in a particularly efficient protocol for wheat described in U.S. Pat. No. 6,153,812, and the references cited therein. Site-specific recombination systems also can be employed to reduce the copy number and random integration of the nucleic acid into the cotton plant genome. For example, the Cre/lox system can be used to immediate lox site-specific recombination in plant cells. This method can be found at least in Choi et al., Nuc. Acids Res. 28:B19, 2000).

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A genetic trait which has been engineered into a particular wheat plant using transformation techniques could be moved into another line using traditional breeding techniques that are well known in the plant breeding arts. For example, a backcrossing approach could be used to move a transgene from a transformed wheat plant to an elite wheat variety and the resulting progeny would comprise a transgene.

Introduction of Transgenes of Agronomic Interest by Transformation. Agronomic genes can be expressed in transformed plants. For example, plants can be genetically engineered to express various phenotypes of agronomic interest, or, alternatively, transgenes can be introduced into a plant by breeding with a plant that has the transgene. Through the transformation of wheat the expression of genes can be modulated to enhance disease resistance, insect resistance, herbicide resistance, water stress tolerance and agronomic traits as well as grain quality traits. Transformation also can be used to insert DNA sequences which control or help control male-sterility. DNA sequences native to wheat as well as non-native DNA sequences can be transformed into wheat and used to modulate levels of native or non-native proteins. Anti-sense technology, various promoters, targeting sequences, enhancing sequences, and other DNA sequences can be inserted into the wheat genome for the purpose of modulating the expression of proteins. Exemplary genes implicated in this regard include, but are not limited to, those categorized below.

1. Genes that Confer Resistance to Pests or Disease:

(A) Plant defenses are often activated by specific interaction between the product of a disease resistance gene (R) in the plant and the product of a corresponding avirulence (Avr) gene in the pathogen. A plant variety can be transformed with a cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., *Science* 262: 1432 (1993) (tomato Pto gene for resistance to *Pseudomonas syringae* pv. tomato encodes a protein kinase); Mindrinos et al., Cell 78:1089, 1994 (Arabidopsis RSP2 gene for resistance to *Pseudomonas syringae*).

*Fusarium* head blight along with deoxynivalenol both produced by the pathogen *Fusarium graminearum* Schwabe have caused devastating losses in wheat production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavoniods, lactoferricin. During infection with *Fusarium graminearum* deoxynivalenol is produced. There is evidence that production of deoxynivalenol increases the virulence of the disease. Genes with properties for detoxification of deoxynivalenol (Adam and Lemmens, In International Congress on Molecular Plant-Microbe Interactions, 1996; McCormick et al. Appl. Environ. Micro. 65:5252-5256, 1999) have been engineered for use in wheat. A synthetic peptide that competes with deoxynivalenol has been identified (Yuan et al., Appl. Environ. Micro. 65:3279-3286, 1999). Changing the ribosomes of the host so that they have reduced affinity for deoxynivalenol also has been used to reduce the virulence of the *Fusarium graminearum.*

Genes used to help reduce *Fusarium* head blight include but are not limited to Tri101(Fusarium), PDR5 (yeast), tip-1 (oat), tip-2(oat), leaf tip-1 (wheat), tip (rice), tip-4 (oat), endochitinase, exochitinase, glucanase (Fusarium), permatin (oat), seed hordothionin (barley), alpha-thionin (wheat), acid glucanase (alfalfa), chitinase (barley and rice), class beta II-1,3-glucanase (barley), PR5/tip (arabidopsis), zeamatin (maize), type 1 RIP (barley), NPR1 (arabidopsis), lactoferrin (mammal), oxalyl-CoA-decarboxylase (bacterium), IAP (baculovirus), ced-9 (*C. elegans*), and glucanase (rice and barley).

(B) A gene conferring resistance to a pest, such as Hessian fly, wheat, stem soft fly, cereal leaf beetle, and/or green bug, for example, the H9, H10, and H21 genes.

(C) A gene conferring resistance to disease, including wheat rusts, *septoria tritici, septoria nodorum*, powdery mildew, *helminthosporium* diseases, smuts, bunts, *fusarium* diseases, bacterial diseases, and viral diseases.

(D) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Manassas, Va.), for example, under ATCC Accession Nos. 40098, 67136, 31995 and 31998.

(E) An insect-specific hormone or pheromone such as an ecdysteroid and juvenile hormone, a variant thereof, a mimetic based thereon, or an antagonist or agonist thereof. See, for example, the disclosure by Hammock et al., Nature 344:458, 1990, of baculovirus expression of cloned juvenile hormone esterase, an inactivator of juvenile hormone.

(F) An insect-specific peptide or neuropeptide which, upon expression, disrupts the physiology of the affected pest. For example, see the disclosures of Regan, J. Biol. Chem. 269:9, 1994 (expression cloning yields DNA coding for insect diuretic hormone receptor), and Pratt et al., Biochem. Biophys. Res. Comm. 163:1243, 1989 (an allostatin is identified in *Diploptera puntata*). See also U.S. Pat. No. 5,266,317 to Tomalski et al., who disclose genes encoding insect-specific, paralytic neurotoxins.

(G) An enzyme responsible for an hyperaccumulation of a monterpene, a sesquiterpene, a steroid, hydroxamic acid, a phenylpropanoid derivative or another non-protein molecule with insecticidal activity.

(H) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., Plant Molec. Biol 21:673, 1993, who provide the nucleotide sequence of the parsley ubi4-2 polyubiquitin gene.

(I) A molecule that stimulates signal transduction. For example, see the disclosure by Botella et al., Plant Molec. Biol. 24:757, 1994, of nucleotide sequences for mung bean calmodulin cDNA clones, and Griess et al., Plant Physiol. 104:1467, 1994, who provide the nucleotide sequence of a maize calmodulin cDNA clone.

(J) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference for this purpose.

(K) A membrane permease, a channel former or a channel blocker. For example, see the disclosure by Jaynes et al., Plant Sci. 89:43, 1993, of heterologous expression of a cecropin-beta lytic peptide analog to render transgenic tobacco plants resistant to *Pseudomonas solanacearum.*

(L) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451, 1990. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(M) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland, 1994 (enzymatic inactivation in transgenic tobacco via production of single-chain antibody fragments).

(N) A virus-specific antibody. See, for example, Tavladoraki et al., Nature 366:469, 1993, who show that transgenic plants expressing recombinant antibody genes are protected from virus attack.

(O) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10:1436, 1992. The cloning and characterization of a gene which encodes a bean endopolygalacturonase-inhibiting protein is described by Toubart et al., Plant J. 2:367, 1992.

(P) A developmental-arrestive protein produced in nature by a plant. For example, Logemann et al., Bio/Technology 10:305, 1992, have shown that transgenic plants expressing the barley ribosome-inactivating gene have an increased resistance to fungal disease.

(Q) Genes involved in the Systemic Acquired Resistance (SAR) Response and/or the pathogenesis related genes. Briggs, Current Biology, 5(2), 1995.

(R) Antifungal genes (Cornelissen and Melchers, Plant Physiol. 101:709-712, 1993; Parijs et al., Planta 183:258-264, 1991; and Bushnell et al., Can. J. of Plant Path. 20:137-149, 1998).

(S) Detoxification genes, such as for fumonisin, beauvericin, moniliformin and zearalenone and their structurally related derivatives. For example, see U.S. Pat. No. 5,792,931.

(T) Cystatin and cysteine proteinase inhibitors.

(U) Defensin genes. See WO03000863.

(V) Genes conferring resistance to nematodes. See WO 03/033651 and Urwin et. al., Planta 204:472-479, 1998.

2. Genes that Confer Resistance to an Herbicide:

(A) Acetohydroxy acid synthase, which has been found to make plants that express this enzyme tolerant to multiple types of herbicides, has been introduced into a variety of plants (see, e.g., Hattori et al., Mol Gen Genet. 246:419, 1995). Other genes that confer tolerance to herbicides include: a gene encoding a chimeric protein of rat cytochrome P4507A1 and yeast NADPH-cytochrome P450 oxidoreductase (Shiota et al., Plant Physiol. 106:17, 1994), genes for glutathione reductase and superoxide dismutase (Aono et al., Plant Cell Physiol 36:1687, 1995) and genes for various phosphotransferases (Datta et al., Plant Mol Biol. 20:619, 1992).

(B) A herbicide that inhibits the growing point or meristem, such as an imidazalinone or a sulfonylurea. Exemplary genes in this category code for mutant ALS and AHAS enzyme as described, for example, by Lee et al., EMBO J. 7: 1241, 1988, and Miki et al., Theor. Appl. Genet. 80: 449, 1990, respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(C) Glyphosate (tolerance, or resistance, imparted by mutant 5-enolpyruv1-3-phosphikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. In U.S. Pat. No. 5,627,061 to Barry et al. describes genes encoding EPSPS enzymes. In U.S. 2002/0062503 A1 Chen et al. describe a wheat plant tolerant to glyphosate. The DNA construct pMON30139 was inserted in wheat via transformation and contains the EPSPS gene as well as other elements. See also U.S. Pat. Nos. 6,248,876 B1; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 00/66746; WO 01/66704; and WO 00/66747, which are incorporated herein by reference for this purpose. Glyphosate resistance also is imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Application Ser. Nos. 60/244,385; 60/377,175 and 60/377,719.

A DNA molecule encoding a mutant aroA gene can be obtained under ATCC accession No. 39256, and the nucleotide sequence of the mutant gene is disclosed in U.S. Pat. No. 4,769,061 to Comai. European Patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., Bio/Technology 7: 61, 1989, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Vasil et al. (Bio/Technology 10:667, 1992) reported developing wheat plants tolerant to glufosinate via particle bombardment and the use of bar genes. The use of bar genes also has resulted in the resistance to the herbicide bialaphos. Exemplary of genes conferring resistance to phenoxy propionic acids and cycloshexones, such as sethoxydim and haloxyfop, are the Acc1-S1, Acc1-S2 and Acc1-S3 genes described by Marshall et al., Theor. Appl. Genet. 83:435, 1992.

(D) A herbicide that inhibits photosynthesis, such as a triazine (psbA and gs+genes) and a benzonitrile (nitrilase gene). Przibilla et al., Plant Cell 3:169, 1991, describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285:173, 1992.

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are tolerant to these herbicides are described in U.S. Pat. Nos. 6,288,306 B1; 6,282,837 B1; and 5,767,373; and international publication WO 01/12825, which are incorporated herein by reference for this purpose.

3. Genes that Confer or Improve Grain Quality:

(A) The content of high-molecular-weight gluten subunits (HMW-GS). Genomic clones have been isolated for different HMW subunits (Anderson et al., In Proceedings of the 7$^{th}$ International Wheat Genetics Symposium, IPR, pp. 699-704, 1988; Shewry et al. In Oxford Surveys of Plant Molecular and Cell Biology, pp. 163-219, 1989; Shewry et al. Journal of Cereal Sci. 15:105-120, 1992). Blechl et al. (J. Plant Phys. 152: 703-707, 1998) have transformed wheat with genes that encode a modified HMW-GS. See also U.S. Pat. Nos. 5,650,558; 5,914,450; 5,985,352; 6,174,725; and 6,252,134, which are incorporated herein by reference for this purpose.

(B) Modified fatty acid metabolism, for example, by transforming a plant with an antisense gene of stearoyl-ACP desaturase to increase stearic acid content of the plant. See Knultzon et al., Proc. Nat'l. Acad. Sci. USA 89:2624, 1992.

(C) Decreased phytate content, for example introduction of a phytase-encoding gene, would enhance breakdown of phytate, adding more free phosphate to the transformed plant. For example, see Van Hartingsveldt et al., Gene 127:87, 1993, for a disclosure of the nucleotide sequence of an *Aspergillus niger* phytase gene. See also U.S. patent application Ser. Nos. 10/255,817 and 10/042,894 and international publication numbers WO 99/05298, WO 03/027243, and WO 02/059324, which are incorporated herein by reference for this purpose.

(D) Modified carbohydrate composition effected, for example, by transforming plants with a gene coding for an enzyme that alters the branching pattern of starch. See Shiroza et al., J. Bacteriol. 170:810, 1988 (nucleotide sequence of *Streptococcus mutans* fructosyltransferase gene), Steinmetz et al., Mol. Gen. Genet. 200:220, 1985 (nucleotide sequence of *Bacillus subtilis* levansucrase gene), Pen et al., Bio/Technology 10:292, 1992 (production of transgenic plants that express *Bacillus licheniformis* alpha-amylase), Elliot et al., Plant Molec. Biol. 21:515, 1993 (nucleotide sequences of tomato invertase genes), Søgaard et al., J. Biol. Chem. 268:22480, 1993 (site-directed mutagenesis of barley alpha-amylase gene), and Fisher et al., Plant Physiol. 102: 1045, 1993 (maize endosperm starch branching enzyme II).

4. Genes that Control Male Sterility (A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene (Paul et al., Plant Mol. Biol. 19:611-622, 1992).

5. Genes that Confer Agronomic Enhancements, Nutritional Enhancements, or Industrial Enhancements.

(A) Improved tolerance to water stress from drought or high salt water condition. The HVA1 protein belongs to the group 3 LEA proteins that include other members such as wheat pMA2005, cotton D-7, carrot Dc3, and rape pLEA76. These proteins are characterized by 11-mer tandem repeats of amino acid domains which may form a probable amphophilic alpha-helical structure that presents a hydrophilic surface with a hydrophobic stripe. The barley HVA1 gene and the wheat pMA2005 gene are highly similar at both the nucleotide level and predicted amino acid level. These two monocot genes are closely related to the cotton D-7 gene and carrot Dc3 gene with which they share a similar structural gene organization. There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried and Walker-Simmons, 1993). Studies on several indica varieties of rice showed that the levels of group 2 LEA proteins (also known as dehydrins) and group 3 LEA proteins in roots were significantly higher in salt-tolerant varieties compared with sensitive varieties. The barley HVA1 gene was transformed into wheat. Transformed wheat plants showed increased tolerance to water stress, (Sivamani et al. Plant Science 155:1-9, 2000, and U.S. Pat. No. 5,981,842.)

(B) Another example of improved water stress tolerance is through increased mannitol levels via the bacterial mannitol-1-phosphate dehydrogenase gene. To produce a plant with a genetic basis for coping with water deficit, Tarczynski et al. (Proc. Natl. Acad. Sci. USA, 89:2600, 1992; WO 92/19731, published No. 12,1992; Science 259:508, 1993) introduced the bacterial mannitol-1-phosphate dehydrogenase gene, mt1D, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski et al. compared the growth of transgenic plants to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level. See also U.S. Pat. No. 5,780,709 and international publication WO 92/19731 which are incorporated herein by reference for this purpose.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick and Thompson, eds. (CRC Press, Inc., Boca Raton, 1993) pp. 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The transgenes described above also can be introduced into a glyphosate-tolerant plant of the present invention by conventional breeding using as one parent a plant that has the transgene of interest.

Mutagenesis of Glyphosate-Tolerant Plants of the Invention. Further embodiments of the invention are the treatment of a glyphosate-tolerant wheat genotype of the invention with a mutagen and the plant produced by such mutagenesis. Information about mutagens and mutagenizing seeds or pollen are presented in the IAEA's *Manual on Mutation Breeding* (IAEA, 1977) other information about mutation breeding in wheat can be found in C. F. Konzak, "Mutations and Mutation Breeding" chapter 7B, of *Wheat and Wheat Improvement*, 2$^{nd}$ edition, ed. Heyne, 1987.

Backcross Conversion. A further embodiment of the invention is a backcross conversion of the glyphosate-tolerant wheat genotypes of the invention. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in "Hybrid Wheat by K. A. Lucken (pp. 444-452 In *Wheat and Wheat Improvement*, ed. Heyne, 1987). Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), Powdery Mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtID). The trait of interest is transferred from the donor parent to the recurrent parent, in this case, the wheat plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Another embodiment of this invention is a method of developing a backcross conversion of a wheat plant of the glyphosate-tolerant wheat genotypes of the invention that involves the repeated backcrossing to one of the glyphosate-tolerant wheat genotypes of the invention or to another selected wheat variety. The number of backcrosses made may be 2, 3, 4, 5, 6 or greater, and the specific number of backcrosses used will depend upon the genetics of the donor parent and whether molecular markers are utilized in the backcrossing program. See, for example, R. E. Allan, "Wheat" in *Principles of Cultivar Development*, Fehr, W. R. Ed. (Macmillan Publishing Company, New York, 1987) pages 722-723, incorporated herein by reference. Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90% 91%, 92%, 93%, 94%, 95%, 96%, 97%, 98%, or 99% of the genetic profile of a desired wheat variety or genotype used for backcrossing. The percentage of the genetics retained in the backcross conversion may be measured by either pedigree analysis or through the use of genetic techniques such as molecular markers or electrophoresis. In pedigree analysis, on average 50% of the starting germplasm would be passed to the progeny line after one cross to another line, 75% after backcrossing once, 87.5% after backcrossing twice, and so on. Molecular markers also could be used to confirm and/or determine the recurrent parent used. The backcross conversion developed from this method may be similar to that of the recurrent parent. Such similarity may be measured by a side by side phenotypic comparison, with differences and similarities determined at a 5% significance level. Any such comparison should be made in environmental conditions that account for the trait being transferred.

Essentially Derived Varieties. Another embodiment of the invention is an essentially derived variety of any of the glyphosate-tolerant wheat genotypes of the invention. As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of any of the glyphosate-tolerant wheat genotypes of the invention is further defined as one whose production requires the repeated use of such a wheat genotype or is predominately derived from such a wheat genotype (International Convention for the Protection of New Varieties of Plants, as amended on Mar. 19, 1991, Chapter V, Article 14, Section 5(c)).

Plant Breeding. This invention also is directed to methods for using the glyphosate-tolerant wheat genotypes of the invention in plant breeding.

One such embodiment is the method of crossing one of the glyphosate-tolerant wheat genotypes of the invention with another variety of wheat to form a first generation population of $F_1$ plants. The population of first generation $F_1$ plants produced by this method also is an embodiment of the invention. This first generation population of $F_1$ plants will comprise an essentially complete set of the alleles of the selected wheat genotype of the invention. One of ordinary skill in the art can utilize either breeder books or molecular methods to identify a particular $F_1$ plant produced in this fashion, and any such individual plant also is encompassed by this invention. These embodiments also cover use of transgenic or backcross conversions of one of the glyphosate-tolerant wheat genotypes of the invention to produce first generation $F_1$ plants.

Another embodiment of the invention is a method of developing a progeny wheat plant comprising crossing one of the glyphosate-tolerant wheat genotypes of the invention with a second wheat plant. A specific method for producing a line derived from one of the glyphosate-tolerant wheat genotypes of the invention is as follows. One of ordinary skill in the art would cross one of the glyphosate-tolerant wheat genotypes of the invention with another variety of wheat, such as an elite variety. The $F_1$ seed derived from this cross would be grown to form a homogeneous population. The $F_1$ seed would contain one set of the alleles from the selected glyphosate-tolerant wheat genotype of the invention and one set of the alleles from the other wheat variety. The $F_1$ genome would be made-up of 50% of the selected glyphosate-tolerant wheat genotypes of the invention and 50% of the elite variety. The $F_1$ seed would be grown and allowed to self, thereby forming $F_2$ seed. On average the $F_2$ seed would have derived 50% of its alleles from the selected glyphosate-tolerant wheat genotype of the invention and 50% from the other wheat variety, but various individual plants from the population would have a much greater percentage of their alleles derived from the selected glyphosate-tolerant wheat genotype of the invention (Wang J. and R. Bernardo, 2000, Crop Sci. 40:659-665 and Bernardo, R. and A. L. Kahler, 2001, Theor. Appl. Genet 102:986-992). The $F_2$ seed would be grown and selection of plants would be made based on visual observation and/or measurement of traits. The progeny that exhibit one or more of the desired traits derived from the selected glyphosate-tolerant wheat genotype of the invention, such as glyphosate tolerance, would be selected and each plant would be harvested separately. This $F_3$ seed from each plant would be grown in individual rows and allowed to self. Then selected rows or plants from the rows would be harvested and threshed individually. The selections would again be based on visual observation and/or measurements for desirable traits of the plants, such as glyphosate tolerance. The process of growing and selection would be repeated any number of times until a homozygous wheat plant derived from the selected glyphosate-tolerant wheat genotype of the invention is obtained. The homozygous wheat plant would contain desirable traits derived from the selected glyphosate-tolerant wheat genotype of the invention, some of which may not have been expressed by the other original wheat variety to which the selected glyphosate-tolerant wheat genotype of the invention was crossed and some of which may have been expressed by both wheat varieties but now would be at a level equal to or greater than the level expressed in the selected glyphosate-tolerant wheat genotype of the invention. The homozygous wheat plants thus obtained would have, on average, 50% of their genes derived from the selected glyphosate-tolerant wheat genotype of the invention, but various individual plants from the population would have a much greater percentage of their alleles derived from the selected glyphosate-tolerant wheat genotype of the invention. The breeding process, of crossing, selfing, and selection may be repeated to produce another population of wheat plants with, on average, 25% of their genes derived from the selected glyphosate-tolerant wheat genotype of the invention, but various individual plants from the population would have a much greater percentage of their alleles derived therefrom. Another embodiment of the invention is a homozygous wheat plant that has received one or more traits, including but not limited to glyphosate tolerance, derived from one of the glyphosate-tolerant wheat genotypes of the invention.

The previous example can be modified in numerous ways, for instance selection may or may not occur at every selfing generation, selection may occur before or after the actual self-pollination process occurs, or individual selections may be made by harvesting individual spikes, plants, rows or plots at any point during the breeding process described. In addition, double haploid breeding methods may be used at any step in the process. The population of plants produced at each and any generation of selfing also is an embodiment of the invention, and each such population would consist of plants containing approximately 50% of its genes from the selected glyphosate-tolerant wheat genotype of the invention, 25% of its genes from the selected glyphosate-tolerant wheat genotype of the invention in the second cycle of crossing, selfing, and selection, 12.5% of its genes from the selected glyphosate-tolerant wheat genotype of the invention in the third cycle of crossing, selfing, and selection, and so on.

Another embodiment of this invention is the method of obtaining a homozygous wheat plant derived from a glyphosate-tolerant wheat genotype of the invention by crossing the selected glyphosate-tolerant wheat genotype of the invention with another variety of wheat and applying double haploid methods to the $F_1$ seed or $F_1$ plant or to any generation of wheat obtained by the selfing of this cross.

Still further, this invention also is directed to methods for producing wheat plants derived from a selected glyphosate-tolerant wheat genotype of the invention by crossing the selected glyphosate-tolerant wheat genotype with a wheat plant and growing the progeny seed, and repeating the crossing or selfing along with the growing steps with the selected glyphosate-tolerant wheat genotype of the invention from 1 to 2 times, 1 to 3 times, 1 to 4 times, or 1 to 5 times. Thus, any and all methods using the glyphosate-tolerant wheat genotypes of the invention in breeding are part of this invention, including selfing, pedigree breeding, backcrossing, hybrid production and crosses to populations. Unique starch profiles, molecular marker profiles and/or breeding records can be used by those of ordinary skill in the art to identify the progeny lines or populations derived from these breeding methods.

In addition, this invention also encompasses progeny with the same or greater glyphosate tolerance, yield, drought tolerance, and/or resistance to lodging as a glyphosate-tolerant wheat genotype of the invention. The expression of these traits may be measured by a side by side phenotypic comparison, with differences and similarities determined at a 5% significance level. Any such comparison should be made in the same environmental conditions.

The invention will be better understood by reference to the following Examples, which are intended to merely illustrate the best mode now known for practicing the invention. The scope of the invention is not to be considered limited thereto.

Example 1

Glyphosate Resistant Mutants Isolated from Large-Scale Screening Efforts

Large-scale glyphosate resistant screening efforts were conducted on mutagenized wheat plants in the greenhouse and field in 2006 (Table 1). In the greenhouse evaluation, 349,000 bulk M2 plants from four spring wheat varieties mutagenized with EMS were evaluated for resistance to glyphosate using both spray application and hydroponics. Of these, 20 plants were tolerant to glyphosate; however, none of the M3 progeny survived re-testing at 18 oz/A Roundup ULTRA™. A field evaluation of 1.5 million M2 plants from Louise, Hollis, Tara 2002 and Macon was conducted at Spillman Farm in Pullman, Wash. during June of 2006. M2 wheat plants were sprayed twice with glyphosate: 1) June 2 with 6 oz/A Roundup ULTRA™; and 2) June 20 with 9 oz/A Roundup ULTRA™. A total of 157 M2 plants survived (Table 1). These putative glyphosate tolerant plants were transplanted from the field to the greenhouse on June $29^{th}$, and resulting M3 from each self-pollinated line was harvested in August. Re-tests of these M3 plants with 18 oz/A Roundup ULTRA™ have been conducted. Of the M3s, 74 show varying degrees of tolerance to glyphosate (Table 1). Among the M3 families with a high percentage of survivors, plants also have been placed in classes based on fitness as crossing parents for breeding efforts. Plants with weak plant vigor or slow growth rates following glyphosate treatment were removed from consideration as viable glyphosate resistant candidates. For example, both LouiseFR1-04 and LouiseFR1-05 had a high % survival; however, LouiseFR1-04 was healthy and normal in phenotype, whereas LouiseFR1-04 had an undesirable short, bushy appearance will limit reproductive potential.

TABLE 1

Number of EMS mutagenized M2 wheat plants screened for tolerance to glyphosate herbicide in greenhouse and field trials in 2005 and 2006.

| | Greenhouse 2005 | Greenhouse 2006 | Field 2006 |
|---|---|---|---|
| Number of M2 plants screened | 265,000 | 349,000 | 1.5 million |
| Application rate of Roundup ULTRA | 18 oz/A | 9 oz/A | 1st application: 6 oz/A 2nd application: 9 oz/A |
| Putative number of glyphosate tolerant M2 plants identified | 4 | 20 | 157 |

TABLE 1-continued

Number of EMS mutagenized M2 wheat plants screened for tolerance to glyphosate herbicide in greenhouse and field trials in 2005 and 2006.

| | Greenhouse 2005 | Greenhouse 2006 | Field 2006 |
|---|---|---|---|
| M3 families with some level of glyphosate tolerance | 1 "GT-Louise" | 0 | 74 |

Re-test data for M3 progeny from putative M2 survivors also is presented.

Survival data (survived=glyphosate tolerant or resistant; dead=glyphosate sensitive or susceptible) for individuals from M3 families that were sprayed once with 18 oz/A Roundup ULTRA™ at the three-leaf stage are reported in Tables 2, 3, 4 and 5. Chi-square ($X^2$) statistical analysis, which tests goodness of fit of expected to observed segregation ratios, was used to analyze survival data to determine whether the glyphosate resistance in each M3 tested resulted from a single or 2-gene mutation. Re-tests of M4 plants derived from these M3 families with significant chi-square values are listed in Table 6.

TABLE 2

Screening results for M3 plants from Field-Rescued (FR) M2 mutants that were resistant to glyphosate in the 2006 field trial. M3 plants were sprayed once in the greenhouse with 18 oz/A Roundup ULTRA ™ at the 3-leaf stage. Based on Chi-square analysis, survival data fit ($X^2 < 3.84$) a 3 glyphosate sensitive (died) to 1 glyphosate tolerant (survived) segregation ratio indicating that a single, recessive glyphosate resistance gene is present in each mutant.

| | Observed Values | | | % | Expected Values | | $X^2$ | Phenotypic |
|---|---|---|---|---|---|---|---|---|
| ID | Died[1] | Survived[2] | Total | Survival | Died | Survived | Value | Observations[3] |
| LouiseFR1-04 | 85 | 27 | 112 | 24.11 | 84.00 | 28.00 | 0.05 | Healthy, Normal |
| LouiseFR1-05 | 94 | 37 | 131 | 28.24 | 98.25 | 32.75 | 0.74 | Bushy, Dwarf |
| LouiseFR1-11 | 26 | 6 | 32 | 18.75 | 24.00 | 8.00 | 0.67 | Dwarf |
| LouiseFR1-33 | 74 | 15 | 89 | 16.85 | 66.75 | 22.25 | 3.15 | Healthy, Normal |
| MaconFR1-05 | 114 | 28 | 142 | 19.72 | 106.50 | 35.50 | 2.11 | Healthy, Normal |
| MaconFR1-06 | 32 | 4 | 36 | 11.11 | 27.00 | 9.00 | 3.70 | Dwarf |
| MaconFR1-07 | 16 | 3 | 19 | 15.79 | 14.25 | 4.75 | 0.86 | Few tillers |
| MaconFR1-08 | 20 | 2 | 22 | 9.09 | 16.50 | 5.50 | 2.97 | Variable |
| MaconFR1-09 | 19 | 4 | 23 | 17.39 | 17.25 | 5.75 | 0.71 | Few tillers |
| MaconFR1-14 | 54 | 10 | 64 | 15.63 | 48.00 | 16.00 | 3.00 | Late flowering |
| MaconFR1-19 | 29 | 4 | 33 | 12.12 | 24.75 | 8.25 | 2.92 | Healthy, Normal |
| MaconFR1-20 | 17 | 2 | 19 | 10.53 | 14.25 | 4.75 | 2.12 | Short, Weak |
| TaraFR1-07 | 9 | 4 | 13 | 30.77 | 9.75 | 3.25 | 0.23 | Healthy, Normal |
| TaraFR1-20 | 74 | 15 | 89 | 16.85 | 66.75 | 22.25 | 3.15 | Late flowering |
| LouiseFR1-41 | 29 | 11 | 40 | 27.50 | 30.00 | 10.00 | 0.13 | Healthy, Normal |
| LouiseFR1-45 | 59 | 30 | 89 | 33.71 | 66.75 | 22.25 | 3.60 | Healthy, Normal |
| LouiseFR1-51 | 69 | 20 | 89 | 22.47 | 66.75 | 22.25 | 0.30 | Healthy, Normal |
| LouiseFR1-54 | 59 | 30 | 89 | 33.71 | 66.75 | 22.25 | 3.60 | Healthy, Normal |
| LouiseFR1-56 | 67 | 22 | 89 | 24.72 | 66.75 | 22.25 | 0.00 | Healthy, Normal |
| LouiseFR1-64 | 73 | 16 | 89 | 17.98 | 66.75 | 22.25 | 2.34 | Healthy, Normal |

[1]"Dead" indicates that the plants were susceptible to glyphosate.
[2]"Survived" indicates that the plants were resistant to 18 oz/A Roundup ULTRA ™
[3]"Healthy, Normal" indicates that the plants are phenotypically similar to unmutagenized spring wheat plants. These individuals represent our best examples of single gene mutations generated with EMS that confer high levels of tolerance to glyphosate herbicide.

Segregation data for all genotypes listed in Table 2 fit expected segregation ratios for a single, recessive gene. In each case approximately 75% of the M3 individuals tested were sensitive (i.e. susceptible) to glyphosate, whereas 25% were tolerant (i.e. resistant) to full commercial application rates.

TABLE 3

Screening results for M3 progeny from Field-Rescued (FR) M2 mutants that were resistant to glyphosate in the 2006 field trial. M3 plants were sprayed once in the greenhouse with 18 oz/A Roundup ULTRA ™ at the 3-leaf stage. Based on Chi-square analysis, survival data fit ($X^2 < 3.84$) a 1 glyphosate sensitive (died) to 3 glyphosate tolerant (survived) segregation ratio indicating that a single, dominant glyphosate resistance gene is present in each mutant.

| | Observed values | | | | Expected value | | |
|---|---|---|---|---|---|---|---|
| ID | Died | Survived | Total | Percent Survival | Died | Survived | $X^2$ Value |
| TaraFR1-27 | 6 | 13 | 19 | 68.42 | 4.75 | 14.25 | 0.44 |
| LouiseFR1-50 | 29 | 60 | 89 | 67.42 | 22.25 | 66.75 | 2.73 |
| LouiseFR1-57 | 27 | 62 | 89 | 69.66 | 22.25 | 66.75 | 1.35 |

Segregation data for the three genotypes listed in Table 3 fit expected segregation ratios for a single, dominant gene. In each case approximately 25% of the M3 individuals tested were sensitive (i.e. susceptible) to glyphosate, whereas 75% were tolerant (i.e. resistant) at 18 oz/A rate of RoundUp ULTRAT™.

Survival data for M3 individuals from the twenty-six genotypes listed in Table 4 align with a 15:1 expected segregation ratio for sensitive (susceptible) to tolerant (resistant) plants, which agrees with expectation for a two-gene trait. In each case approximately 93.75% of the M3 individuals tested were sensitive to glyphosate, whereas 6.25% were tolerant to 18 oz/A rate of RoundUp ULTRA™. In this case, recessive mutations in two unique genes may have resulted in enhanced glyphosate tolerance.

Some of our glyphosate tolerant wheat mutants resulted from mutations that occurred in two genes that may be located on the same or different chromosomes. These results indicate that various types of genetic resistance (i.e. single or two gene) to glyphosate can be generated in plants using EMS mutagenesis. They also support the notion that combining multiple glyphosate tolerance genes that individually express tolerance to glyphosate rates below commercial application recommendations can be used in breeding strategies to generate glyphosate resistant cultivars. This strategy also can be used to prevent the spread of glyphosate resistance to weed populations that are wheat relatives (i.e. goatgrass). Transmission of dominant herbicide-resistance genes to weed populations is a serious concern for herbicide resistant crop plants. If glyphosate resistance is the result of one or two recessive mutations, $F_1$ plants resulting from outcrossing to a weed would not survive treatment with glyphosate and would be unlikely to give rise to resistant progeny.

Re-tests of the M3 families with significant chi-square values for a single recessive or single dominant and two-gene recessive or two-gene dominant were carried out in the greenhouse. Results of the re-tests are listed in Table 6. The rate of RoundUp ULTRA™ was increased to 27 oz/A to better align with commercial application recommendations.

TABLE 4

Screening results for M3 progeny of Field-Rescued (FR) M2 mutants that were resistant to glyphosate in the 2006 field trial. M3 plants were sprayed once in the greenhouse with 18 oz/A Roundup ULTRA ™ at the 3-leaf stage. Based on Chi-square analysis, survival data fit ($X^2 < 3.84$) a 15 glyphosate sensitive (died) to 1 glyphosate tolerant (survived) segregation ratio indicating that two recessive glyphosate resistance genes are present in each mutant.

| | Observed values | | | Percent | Expected value | | |
|---|---|---|---|---|---|---|---|
| ID | Died | Survived | Total | Survival | Died | Survived | $X^2$ Value |
| HollisFR1-05 | 34 | 2 | 36 | 5.56 | 33.75 | 2.25 | 0.03 |
| LouiseFR1-02 | 60 | 6 | 66 | 9.09 | 61.88 | 4.13 | 0.91 |
| LouiseFR1-03 | 26 | 1 | 27 | 3.70 | 25.31 | 1.69 | 0.30 |
| LouiseFR1-12 | 87 | 2 | 89 | 2.25 | 83.44 | 5.56 | 2.43 |
| LouiseFR1-16 | 117 | 3 | 120 | 2.50 | 112.50 | 7.50 | 2.88 |
| LouiseFR1-22 | 86 | 3 | 89 | 3.37 | 83.44 | 5.56 | 1.26 |
| LouiseFR1-39 | 84 | 5 | 89 | 5.62 | 83.44 | 5.56 | 0.06 |
| LouiseFR1-40 | 86 | 3 | 89 | 3.37 | 83.44 | 5.56 | 1.26 |
| MaconFR1-01 | 69 | 9 | 78 | 11.54 | 73.13 | 4.88 | 3.72 |
| MaconFR1-02 | 69 | 5 | 74 | 6.76 | 69.38 | 4.63 | 0.03 |
| MaconFR1-04 | 53 | 5 | 58 | 8.62 | 54.38 | 3.63 | 0.56 |
| MaconFR1-16 | 74 | 2 | 76 | 2.63 | 71.25 | 4.75 | 1.70 |
| MaconFR1-16 | 98 | 3 | 101 | 2.97 | 94.69 | 6.31 | 1.85 |
| MaconFR1-18 | 167 | 11 | 178 | 6.18 | 166.88 | 11.13 | 0.00 |
| MaconFR1-21 | 141 | 4 | 145 | 2.76 | 135.94 | 9.06 | 3.02 |
| MaconFR1-22 | 79 | 10 | 89 | 11.24 | 83.44 | 5.56 | 3.78 |
| TaraFR1-12 | 67 | 3 | 70 | 4.29 | 65.63 | 4.38 | 0.46 |
| TaraFR1-14 | 126 | 5 | 131 | 3.82 | 122.81 | 8.19 | 1.32 |
| TaraFR1-16 | 168 | 10 | 178 | 5.62 | 166.88 | 11.13 | 0.12 |
| TaraFR1-17 | 172 | 6 | 178 | 3.37 | 166.88 | 11.13 | 2.52 |
| TaraFR1-24 | 128 | 5 | 133 | 3.76 | 124.69 | 8.31 | 1.41 |
| TaraFR1-25 | 83 | 6 | 89 | 6.74 | 83.44 | 5.56 | 0.04 |
| HollisFR1-11 | 86 | 3 | 89 | 3.37 | 83.44 | 5.56 | 1.26 |
| LouiseFR1-47 | 87 | 2 | 89 | 2.25 | 83.44 | 5.56 | 2.43 |
| LouiseFR1-53 | 82 | 7 | 89 | 7.87 | 83.44 | 5.56 | 0.40 |
| LouiseFR1-58 | 86 | 3 | 89 | 3.37 | 83.44 | 5.56 | 1.26 |

TABLE 5

Screening results for M3 progeny of Field-Rescued (FR) M2 mutants that were resistant to glyphosate in the 2006 field trial. M3 plants were sprayed once in the greenhouse with a 18 oz/A Roundup ULTRA ™ at the three-leaf stage. Based on Chi-square analysis, survival data fit ($X^2 < 3.84$) a 1 glyphosate sensitive (died) to 15 glyphosate tolerant (survived) segregation ratio indicating that two dominant glyphosate resistance genes are present in this mutant.

| | Observed values | | | | Expected value | | |
|---|---|---|---|---|---|---|---|
| ID | Died | Survived | Total | Percent Survival | Died | Survived | $X^2$ Value |
| HollisFR1-9 | 0 | 42 | 42 | 100.00 | 39.38 | 2.63 | 2.80 |

TABLE 6

Screening results for M4 progeny of Field-Rescued (FR) M3 mutants that were resistant to glyphosate in the 2006 greenhouse re-tests, with significant Chi-Square values for single or two-gene models in the M3 generation. M4 plants were sprayed once with 27 oz/A Roundup ULTRA ™ at the 3-leaf stage. Based on Chi-square analysis, survival data fit ($X^2 < 3.84$) expected segregation ratios of glyphosate sensitive (died) to glyphosate tolerant (survived) for 3:1 (single recessive gene), 1:3 (single dominant gene), 1:15 (two dominant genes), or 15:1 (two recessive genes).

| | Expected | Observed values | | | Percent | Expected value | | $X^2$ |
|---|---|---|---|---|---|---|---|---|
| ID | ratio | Died | Survived | Total | Survival | Died | Survived | Value |
| LouiseFR1-22-1 | 3:1 | 28 | 10 | 38 | 26.32 | 28.50 | 9.50 | 0.04 |
| MaconFR1-16-11 | 3:1 | 30 | 8 | 38 | 21.05 | 28.50 | 9.50 | 0.32 |
| MaconFR1-18-5 | 3:1 | 24 | 14 | 38 | 36.84 | 28.50 | 9.50 | 2.84 |
| MaconFR1-19-4 | 3:1 | 31 | 7 | 38 | 18.42 | 28.50 | 9.50 | 0.88 |
| MaconFR1-7-2 | 3:1 | 33 | 5 | 38 | 13.16 | 28.50 | 9.50 | 2.84 |
| TaraFR1-12-2 | 3:1 | 26 | 12 | 38 | 31.58 | 28.50 | 9.50 | 0.88 |
| TaraFR1-20-2 | 1:3 | 33 | 5 | 38 | 86.84 | 28.50 | 9.50 | 2.84 |
| LouiseFR1-33-6 | 1:15 | 37 | 1 | 38 | 97.37 | 35.63 | 2.38 | 0.85 |
| LouiseFR1-3-1 | 15:1 | 34 | 4 | 38 | 10.53 | 35.63 | 2.38 | 1.19 |
| MaconFR1-1-1 | 15:1 | 36 | 2 | 38 | 5.26 | 35.63 | 2.38 | 0.06 |
| MaconFR1-19-3 | 15:1 | 35 | 3 | 38 | 7.89 | 35.63 | 2.38 | 0.18 |
| MaconFR1-21-2 | 15:1 | 36 | 2 | 38 | 5.26 | 35.63 | 2.38 | 0.06 |
| MaconFR1-22-1 | 15:1 | 37 | 1 | 38 | 2.63 | 35.63 | 2.38 | 0.85 |
| MaconFR1-7-2 | 15:1 | 33 | 5 | 38 | 13.16 | 35.63 | 2.38 | 3.09 |
| MaconFR1-8-2 | 15:1 | 34 | 4 | 38 | 10.53 | 35.63 | 2.38 | 1.19 |
| TaraFR1-14-6 | 15:1 | 37 | 1 | 38 | 2.63 | 35.63 | 2.38 | 0.85 |
| TaraFR1-25-6 | 15:1 | 34 | 4 | 38 | 10.53 | 35.63 | 2.38 | 1.19 |
| TaraFR1-7-1 | 15:1 | 35 | 3 | 38 | 7.89 | 35.63 | 2.38 | 0.18 |

In the spring of 2007, field tests were conducted on M4 progeny from Field-Rescued (FR) M3 mutants that were resistant to glyphosate in the 2006 greenhouse re-tests. M4 seed were planted in a plot consisting of three five-foot rows. Glyphosate in the form of Roundup ULTRA was applied on May $24^{th}$, 2007. A rate of 0.84 kg ae/ha (32 oz/A) and a rate of 1.68 kg ae/ha (64 oz/A) was applied using a hooded boom sprayer. Spray nozzles (Teejet XR 80015) were 14 inches apart and 12 inches above the canopy. Plants were at the 5 leaf stage and the 1-2 tiller stage at application. Weather was sunny, 63-65 degree F., 3.5 mph wind from the south changing to the west. Soil temp was 14° C. Survivors were harvested on Jun. 15, 2007 and transplanted to pots in the greenhouse. Transplants included one 32 oz/A survivor each from fifteen FR M4 lines. Six of these M4 lines were derived from the same M3 mutant, TaraFR1-15.

The remaining M4 progeny of FR M3 mutants that were not included in the field tests due to late harvest were retested in the greenhouse using 32 oz/A and 64 oz/A application rates. M5 seed from all M4 survivors were harvested and retested in the field in 2008 with 64 oz/A and 128 oz/A spray rates of glyphosate. Survivors are list under Example 3.

Bulk M2 seed of Louise, Hollis, Tara 2002, Macon, and Zak also were planted in the field at Spillman Agronomy Farm, Pullman, Wash., in the spring of 2007. Approximately 970,000 seed were planted on April $24^{th}$ and resulting seedlings were sprayed with 64 oz/A RoundUp ULTRA on May $18^{th}$. One hundred survivors were transplanted from the field to pots in the greenhouse on June $20^{th}$. Self-pollinated seed from these M2 survivors have been produced. None of the M3 progeny survived re-testing in the field in the spring of 2008 at application rates of 64 oz/A and 128 oz/A.

Genotypes that survive a 64 oz/A rate of glyphosate in field or greenhouse screenings were selected as breeding parents for introgressing glyphosate resistance genes into adapted spring wheat cultivars and are listed in Table 7.

TABLE 7

List of genotypes that tolerate a 64 oz/A treatment of Roundup ULTRA ™ in greenhouse or field tests. These genotypes represent selected breeding candidates based on phenotypic characteristics and/or segregation ratios for either a single recessive gene or two recessive genes for glyphosate resistance.

| | Rationale | |
|---|---|---|
| ID | Phenotype[1] | Segregation Ratios[2] |
| IGT07002-0 | Healthy, Normal | 3:1 |
| IGT07005-No. 1-0 | Intermediate, Normal | 3:1 |
| IGT07006-0 | Healthy, Normal | 3:1 |
| IGT07091-0 | Intermediate, Normal | 3:1 |
| IGT07003-No. 1-0 | Intermediate, Normal | 15:1 |
| IGT07087-0 | Healthy, Normal | 15:1 |
| IGT07092-0 | Intermediate, Normal | 15:1 |
| TaraFR1-20-2 | Healthy, Normal | 15:1 |
| Re-Mut 3.1 M3 Bulk | Intermediate, Normal | 3:1 |
| Re-Mut 3.2 M3 Bulk | Intermediate, Normal | 15:1 |
| Re-Mut 3.3 M3 Bulk | Intermediate, Normal | 3:1 |
| Re-Mut 3.4 M3 Bulk | Intermediate, Normal | 3:1 |

TABLE 7-continued

List of genotypes that tolerate a 64 oz/A treatment of Roundup ULTRA ™ in greenhouse or field tests. These genotypes represent selected breeding candidates based on phenotypic characteristics and/or segregation ratios for either a single recessive gene or two recessive genes for glyphosate resistance.

| ID | Rationale Phenotype[1] | Segregation Ratios[2] |
|---|---|---|
| Re-Mut 3.5 M3 Bulk | Intermediate, Normal | 3:1 |
| MaconFR1-16 M4 Bulk | Intermediate, Normal | 15:1 |
| Re-Mut GTL 3.4-10* | Healthy, Normal | N/A |
| TaraFR1-15-57* | Healthy, Normal | N/A |
| Louise M2 Bulk FR2 1-45* | All Healthy, Normal | N/A |
| Alpowa M2 Bulk FR2 1-32* | 30 Healthy, Normal; 2 Dwarf | N/A |
| Macon M2 Bulk FR2 1-10* | All Healthy, Normal | N/A |
| Louise Double Mutated M2 Bulk FR2 1-13* | All Healthy, Normal | N/A |

[1]"Healthy, Normal" indicates that the plants are phenotypically similar to unmutagenized spring wheat plants; Intermediate indicates that plants are less vigorous than un-mutagenized spring wheat plants, but still appear normal.
[2]Based on Chi-square analysis, survival data fit ($X^2 < 3.84$) ratios of glyphosate sensitive (died) to glyphosate tolerant (survived) of 3:1 (single recessive gene) or 15:1 (two recessive genes).
*These lines were screened in the field at Spillman Farm, Pullman, WA. In order to determine segregation ratios, re-tests are performed in the greenhouse.

Note that in Table 7, Louise M2 Bulk FR2 1-45, Alpowa M2 Bulk FR2 1-32, Macon M2 Bulk FR2 1-10, and Louise Double Mutated M2 Bulk FR2 1-13 represent 100 individual survivors from these M2 Bulks. For example, there were 45 survivors from Louise M2 Bulk FR2s, each named Louise M2 Bulk FR2-1, Louise M2 Bulk FR2-2, and so on.

Example 2

Identification of Enhancers of GT-Louise

The glyphosate tolerant phenotype of GT-Louise, which was only tolerant to a single 9 oz/A application of glyphosate, may be enhanced by creating a mutation in a second gene that allows survival after two 9 oz/A applications of glyphosate. To accomplish this, M4 grain of GT-Louise was re-mutagenized with EMS, and resulting M1 seed from re-mutagenized GT-Louise were advanced to the M2 to screen for enhancer mutations in a second gene that increases glyphosate tolerance levels. Of the 48 GT-Louise M3 seeds re-mutagenized, 43 germinated and were self-pollinated to obtain M2 seed for screening. A total of 13,706 M2 re-mutagenized GT-Louise seeds were planted in the greenhouse, and resulting M2 plants were first sprayed with a 9 oz/A rate of Roundup ULTRA™ at the 2-3 leaf stage. A second application of glyphosate was made seven days later at 9 oz/A Roundup ULTRA™. Of these, 751 M2 plants survived both glyphosate applications, suggesting that these plants may contain a mutation in a second gene conferring enhanced glyphosate tolerance compared to GT-Louise. These M2 plants were allowed to self-pollinate, and resulting M3 progeny will be retested to determine if this increased level of tolerance to glyphosate is heritable. Of the 751 M2 survivors, 57 are considered to be excellent candidates for enhanced tolerance to glyphosate since sprayed leaves from these plants showed only slight injury and continued growing in addition to producing new leaves and tillers, after two 6 oz/A applications of glyphosate. Since the leaves of the original GT-Louise died back after exposure to one 9 oz/A rate of glyphosate and then produced new tillers, these 57 candidates may have a new mutation in a second gene conferring enhanced glyphosate tolerance in sprayed leaves. Of the remaining 694 M2 survivors, 154 are considered better candidates because after the first two leaves died as a result of the spray applications, vigorous re-growth occurred from the crown. This re-growth appears to be more vigorous than that seen in other candidates and in the original GT-Louise.

M3 seed from 396 Re-Mut GTL M2 survivors were screened in a field test in the spring of 2007 as described for the FR mutants in Example 1. Survivors were harvested from the field on June 15$^{th}$ and transplanted to the greenhouse. Transplants included one 32 oz/A survivor each from 20 Re-Mut GTL M3 lines. Individuals from M3 lines derived from the same M2 line also survived the field screening: Re-Mut GTL 3.33-1 had thirteen 32 oz/A survivors, Re-Mut GTL 3.33-8 had three 32 oz/A survivors, and Re-Mut GTL 3.33-11 had four 32 oz/A survivors. M4 seed from M3 were harvested and re-tested using 64 oz/A and 128 oz/A of RoundUp ULTRA™ in greenhouse screens in the fall of 2007 and field screens in the spring of 2008. None of the M4 plants survived re-tests at these rates.

A second approach to enhance levels of tolerance to glyphosate involved crossing GT-Louise to the homoeologus pairing mutant Ph1. In the fall of 2006, crosses were made between GT-Louise and the Ph1 mutant. $F_1$ seed from these crosses were planted and increased to the $F_2$ generation and $F_2$ plants were screened in the greenhouse using 18 oz/A of RoundUp ULTRA™. Survivors were saved from the progeny of two crosses (IGT07004-No. 1 and No. 2) (Table 8) and increased to the $F_3$ generation. $F_3$ plants were re-tested at the 32 oz/A and 64 oz/A spray rates. Survivors were recovered from IGT07004-No. 2-0-1 at the 32 oz/A spray rate. The survival data of both the $F_2$ and $F_3$ of this cross (IGT07004-No. 2) fit a 3:1 glyphosate sensitive (died) to glyphosate tolerant (survived) ratio indicating two recessive genes are present (Table 8).

TABLE 8

Screening results for $F_2$ and $F_3$ progeny of GT-Louise crossed with the Ph1 mutant in 2007 greenhouse tests. $F_2$ plants were sprayed once with 18 oz/A Roundup ULTRA ™ at the 3-leaf stage. $F_3$ plants were sprayed once with 32 oz/A RoundUp ULTRA ™ at the 3-leaf stage. Based on Chi-square analysis, survival data fit ($X^2 < 3.84$) ratios of glyphosate sensitive (died) to glyphosate tolerant (survived) of 3:1 (single recessive gene) for IGT07004-No. 1-0, and 15:1 (two recessive genes) for IGT07004-No. 2-0 and IGT07004-No. 2-0-1.

| ID | Fn | Expected ratio | Observed values Died | Survived | Total | Percent Survival | Expected value Died | Survived | $X^2$ |
|---|---|---|---|---|---|---|---|---|---|
| IGT07004-No. 1-0 | F2 | 15:1 | 62 | 2 | 64 | 3.13 | 60.00 | 4.00 | 1.07 |
| IGT07004-No. 2-0 | F2 | 3:1 | 49 | 15 | 64 | 23.44 | 48.00 | 16.00 | 0.08 |

TABLE 8-continued

Screening results for $F_2$ and $F_3$ progeny of GT-Louise crossed with the Ph1 mutant in 2007 greenhouse tests. $F_2$ plants were sprayed once with 18 oz/A Roundup ULTRA ™ at the 3-leaf stage. $F_3$ plants were sprayed once with 32 oz/A RoundUp ULTRA at the 3-leaf stage. Based on Chi-square analysis, survival data fit ($X^2 < 3.84$) ratios of glyphosate sensitive (died) to glyphosate tolerant (survived) of 3:1 (single recessive gene) for IGT07004-No. 1-0 and, and 15:1 (two recessive genes) for IGT07004-No. 2-0 and IGT07004-No. 2-0-1.

| ID | Fn | Expected ratio | Observed values Died | Survived | Total | Percent Survival | Expected value Died | Survived | $X^2$ |
|---|---|---|---|---|---|---|---|---|---|
| IGT07004-No. 2-0-1 | F3 | 3:1 | 28 | 10 | 38 | 26.32 | 28.50 | 9.50 | 0.04 |

Enhancing Genetic Resistance to Glyphosate

In order to combine unique glyphosate resistance genes into the same genotype, Re-Mut GTL mutants have been hybridized with GT-Louise, as well as each other, and FR mutants in the greenhouse using standard controlled cross-hybridization procedures. Our hope is that the combined effect of two or three glyphosate tolerance genes from unique mutants will provide higher tolerance levels than that provided by either single gene alone.

In the fall and winter of 2006-2007, 147 crosses were made between glyphosate tolerant mutants and labeled "IGT" for increased glyphosate tolerance. $F_1$ hybrids resulting from each cross were self-pollinated to generate segregating $F_2$ progeny for herbicide screening. These $F_2$ progeny were screened with 32 oz/A and 64 oz/A of Roundup ULTRA™ in the greenhouse, and survivors were advanced to the next generation, followed by re-testing in the field in 2008 with 64 oz/A (2×) and 128 oz/A (4×) application rates of Roundup ULTRA™. Survivors of the 2× and 4× application rates of glyphosate are listed under Example 3. The re-testing cycle will be repeated until homozygous resistant lines that withstand 64 oz/A rates of Roundup ULTRA™ are identified.

Another approach to combine unique glyphosate resistance genes in the same genotype involved crossing the FR mutants listed in Table 6 that appear to have single recessive genes, single dominant gene, two recessive genes, and two dominant genes. In the spring of 2007, a crossing block consisting of M4 FR mutants, surviving a 27 oz/A spray of RoundUp ULTRA™, was established. Sixty crosses of a half-diallel mating design were made. Additional crosses were made among 1× and 2× survivors from the IGT lines, Re-Mut GTL lines, and FR1 lines listed in Table 6. These $F_t$ populations were labeled "EGT" for enhanced glyphosate tolerance. The $F_1$ seed were harvested in late summer of 2007 and were advanced to the $F_2$ generation. The $F_2$ were re-tested in the greenhouse and field in the spring of 2008 at application rates of 64 oz/A and 128 oz/A. Survivors from these re-tests are listed under Example 3.

Example 3

Additional Glyphosate-Tolerant Mutants from Field Screening

Five new glyphosate tolerant wheat genotypes were identified as M2 putative mutants in field screening in 2008. These were isolated using the method previously described but using a higher concentration of glyphosate, 3.36 kg acid equivalent per hectare (ae/ha) (4× field rates, 128 oz/A, 3 lbs. ae/A). Isolation numbers are Tara 0.4.1, Tara 0.4.2, Tara 0.4.3, Tara 0.4.4, and Louise FR3-1. The following showed resistance at 64 ounce per acre (oz/A) in greenhouse screenings: Tara 0.4.5 and Tara 0.4.6.

Genotypes identified in field season 2007 were re-examined in the field in 2008. The following genotypes showed survival at 1.68 kg ae/ha (2× field rates, 64 oz/A, 1.5 lb ae/A) glyphosate: Macon FR3-1 M2, GT-Louise, and Louise FR1-62. Only one single-mutation-event genotype showed survival at the 4× field rate (3.36 kg ae/ha glyphosate), Louise FR1-42.

It should be noted that as the genetic background has become cleaner with successive generations and selection, GT-Louise M6 plants are showing survival at 2× field rates (1.68 kg ae/ha). We have determined that GT-Louise accumulated lower levels of shikimic acid over time in response to glyphosate treatment compared to wild-type Louise. This data confirms that the GT-Louise mutation is altering the shikimic acid pathway, the target of glyphosate herbicides. GT-Louise has been backcrossed to a background that is not glyphosate tolerant. $F_2$ segregation analyses from this cross shown in Table 9 below are consistent with a single gene recessive trait.

TABLE 9

$F_2$ segregation analysis from backcrossing GT-Louise to a non-glyphosate-tolerant wheat

| Pedigree | Fn | Ratio | Observed values Died | Survived | Total | Percent survival | Expected value Died | Survived | Chi square |
|---|---|---|---|---|---|---|---|---|---|
| GT-Louise/+ | $F_2$ | 15:1 | 62 | 2 | 64 | 3.1 | 60 | 4 | 1.07* |
| GT-Louise/+ | $F_2$ | 3:1 | 49 | 15 | 64 | 23.4 | 48 | 16 | 0.08* |
| GT-Louise/+ | $F_3$ | 3:1 | 28 | 10 | 38 | 26.3 | 28.5 | 9.5 | 0.04* |
| GT-Louise | M5 | 3:1 | 48 | 16 | 64 | 25.0 | 48 | 16 | 0.00* |

TABLE 9-continued

F₂ segregation analysis from backcrossing GT-Louise to a non-glyphosate-tolerant wheat

| Pedigree | Fn | Ratio | Observed values | | Total | Percent survival | Expected value | | Chi square |
|---|---|---|---|---|---|---|---|---|---|
| | | | Died | Survived | | | Died | Survived | |
| GT-Louise | M5 | 15:1 | 57 | 7 | 64 | 10.9 | 60 | 4 | 2.40* |

Progress has been made in improving glyphosate tolerance to higher concentrations of glyphosate by crossing independent glyphosate tolerant gentoypes to one another, that is, by "gene pyramiding". Many genotypes were identified as providing consistent resistance at 1× and 2× application rates in the greenhouse and used for crosses. These lines include but are not restricted to: GT-Louise, Louise FR1-33-6, Louise FR1-65-2, Louise FR1-43, Hollis FR1-9-14, Tara FR1-15-94-(alias Neo), Tara FR1-20-2 and their progeny. F₂ plants from crosses (EGT populations) resulting in survival of 1.68 kg ae/ha (2×) in the 2008 field screening include: EGT07073-0, EGT07081-0, EGT07100-0, EGT07111-0, EGT07118-0, EGT07130-0, EGT07132-0, EGT07138-0, EGT07139-0, EGT07140-0, EGT07143-0, EGT07146-0, EGT07149-0, EGT07154-0, EGT07155-0, EGT07156-0, EGT07158-0, and EGT070180-0. F₂ plants from crosses (EGT populations) resulting in survival of 1.68 kg ae/ha (2×) in the 2008 greenhouse screening include: EGT07012, EGT07089, and EGT07194. F₃ plants from crosses (IGT populations) resulting in survival of 1.68 kg ae/ha (2×) in the 2008 field screening include: IGT07011-0-0, IGT07013-0-0, IGT07028-0-0, IGT07029-0-0, IGT07064-0-0, IGT07073-0-0. F₃ plants from crosses (IGT populations) resulting in survival of 1.68 kg ae/ha (2×) in the 2008 greenhouse screening include: IGT07041-0-0, IGT07050-0-0, and IGT07073-0-0. F₂ plants from crosses (EGT populations) resulting in survival of 3.36 kg ae/ha (4×) in the 2008 field screening include: EGT07162-0, F₃ plants from crosses (IGT populations) resulting in survival of 3.36 kg ae/ha (4×) in the 2008 field screening include: IGT07022-0-0, IGT07027-0-0, IGT07030-0-0, IGT07031-0-0, and IGT07074-0-0.

Example 4

Breeding Plan for the Recovered Glyphosate Resistance Mutants

Based on genetic segregation data among progeny of self-pollinated mutants, several glyphosate tolerant (GT) lines identified through this research may have single gene or two gene resistance mechanisms. As a result, the following results are expected.

One-Gene Models for Genetic Resistance to Glyphosate Herbicide a. Glyphosate Resistance is Conferred by a Single Dominant Gene: One would expect a 3 (75%) to 1 (25%) segregation ratio of alive to dead individuals among self-pollinated progeny from a heterozygous plant when sprayed with a 1× commercial application rate of glyphosate.

b. Glyphosate Resistance is Conferred by a Single Recessive Gene: One would expect a 1 (25%) to 3 (75%) segregation ratio of alive to dead individuals among self-pollinated progeny from a heterozygous plant when sprayed with a 1× commercial application rate of glyphosate.

c. Glyphosate Resistance is Conferred by a Single Semi-Dominant (Additive) Gene: One would expect a 1 (25%) to 2 (50%) to 1 (25%) segregation ratio of alive to intermediate (i.e. slow dying or tolerant to reduced herbicide rates) to dead individuals among self-pollinated progeny from a heterozygous plant when sprayed with a 1× commercial application rate of glyphosate.

Two-Gene Models for Genetic Resistance to Glyphosate Herbicide a. Glyphosate Resistance is Conferred by a Two Dominant Genes: One would expect a 15 (93.75%) to 1 (6.25%) segregation ratio of alive to dead individuals among self-pollinated progeny from a heterozygous plant when sprayed with a 1× commercial application rate of glyphosate.

b. Glyphosate Resistance is Conferred by a Two Recessive Genes: One would expect a 1 (6.25%) to 15 (93.75%) segregation ratio of alive to dead individuals among self-pollinated progeny from a heterozygous plant when sprayed with a 1× commercial application rate of glyphosate.

c. Glyphosate Resistance is Conferred by a One Dominant Gene and One Recessive Gene: One would expect a 3 (18.75%) to 13 (62.50%) to 3 (18.75%) segregation ratio of alive to intermediate (i.e. slow dying or tolerate reduced herbicide rates) to dead individuals among self-pollinated progeny from a heterozygous plant when sprayed with a 1× commercial application rate of glyphosate.

Deploying Effective Single or Two-Gene Resistances to Glyphosate

For commercial cultivation, it is preferable that glyphosate tolerant wheat varieties survive 1× to 2× (32 oz/A and 64 oz/A of Roundup Ultra®, respectively) of the recommended application rates in the field due to concerns with overspray when herbicide is applied in passes using tractor or aerial application methods. For glyphosate tolerant genes that confer resistance to commercial applications rates of Roundup Ultra®, genes are deployed into adapted spring wheat germplasm using the following strategies.

Deploying Single Gene Resistance to Glyphosate Herbicide a. Glyphosate Resistance is Conferred by a Single Dominant Gene: An adapted line (glyphosate susceptible) is cross-hybridized to a glyphosate tolerant mutant line. Seed are planted and resulting F₁ hybrid plants are sprayed with 32 oz/A Roundup Ultra® to confirm that the resistance gene was transmitted during the crossing process. Surviving F₁ plants are allowed to self-pollinate and resulting F₂ seed are harvested. Seed are planted and resulting F₂ plants are sprayed with 32 oz/A Roundup Ultra®. Seventy-five percent of the F₂ progeny are expected to survive. Survivors are self-pollinated and resulting F₃ seed are harvested. F₃ plants are screened with 32 oz/A of Roundup Ultra® to identify individuals that are homozygous for the dominant glyphosate resistance gene. All F₃ progeny from homozygous F₂ plants with the dominant glyphosate resistance gene will survive commercial application rates of glyphosate. If segregation for survival occurs, the $F_2$ individual from which the $F_3$ family was generated was heterozygous for the glyphosate resistance gene. Homozygous $F_2$ or $F_3$ plants are used as donor parents for introgressing the gene into adapted germplasm through backcross breeding or as a parent of traditional forward breeding crosses. Commercial rates of Roundup Ultra® are used for screening purposes during every generation of advancement, regardless of which gene deployment strategy is used to ensure that the resistance gene has been transmitted and/or the gene is present in the homozygous state.

b. Glyphosate Resistance is Conferred by a Single Recessive Gene: An adapted line (glyphosate susceptible) is cross-hybridized to a glyphosate tolerant mutant line. Seed are planted; however, resulting $F_1$ hybrid plants with not be sprayed with glyphosate since the recessive gene are masked in the heterozygous state (i.e. the hybrids are susceptible to glyphosate). $F_2$ seed are harvested from self-pollinated $F_1$ plants, which are planted in the greenhouse. $F_2$ plants are sprayed with 32 oz/A Roundup Ultra®. Twenty-five percent of the $F_2$ progeny that are expected to be homozygous for the recessive glyphosate resistance gene will survive the glyphosate treatment. Survivors are allowed to self-pollinate to produce $F_3$ seed for planting. Resulting $F_3$ plants are sprayed with 32 oz/A of Roundup Ultra® to identify individuals that are homozygous for the recessive glyphosate resistance gene. All $F_3$ progeny from surviving $F_2$ plants will survive commercial application rates of glyphosate. Homozygous $F_2$ or $F_3$ plants are used as donor parents for introgressing the gene into adapted germplasm through backcross breeding or as a parent of traditional forward breeding crosses. After each generation of crossing, resulting hybrids are self-pollinated, and resulting progeny should be screened with commercial rates of Roundup Ultra® to ensure that the recessive resistance gene is present in the homozygous state.

c. Glyphosate Resistance is Conferred by a Single Semi-Dominant (Additive) Gene: With an additive gene of this nature, the highest expression level of resistance to glyphosate is expected when the dominant gene is present in the homozygous state. Therefore, the strategy proposed in "a" above are used to deploy this gene.

Deploying Two-Gene Resistance to Glyphosate Herbicide a. Glyphosate Resistance is Conferred by a Two Dominant Genes: An adapted line (glyphosate susceptible) is cross-hybridized to a glyphosate tolerant mutant line. Resulting seed are planted in the greenhouse, and resulting $F_1$ hybrid plants are sprayed with 32 oz/A Roundup Ultra® to confirm that the resistance genes were transmitted during the crossing process. $F_2$ seed are harvested from surviving $F_1$ plants, which are sown into flats in the greenhouse. $F_2$ plants are sprayed with 32 oz/A Roundup Ultra®. We expect 93.75% of the $F_2$ progeny to survive. Self-pollinated seed from survivors are harvested, and resulting $F_3$ plants are screened with 32 oz/A Roundup Ultra® to identify individuals that are homozygous for the dominant glyphosate resistance genes. All $F_3$ progeny from homozygous $F_2$ plants with the dominant glyphosate resistance genes will survive commercial application rates of glyphosate. If segregation for survival occurs, the $F_2$ individual from which the $F_3$ family was generated was heterozygous for one or both of the glyphosate resistance gene. Homozygous $F_2$ or $F_3$ are used as donor parents for introgressing the gene into adapted germplasm through backcross breeding or as a parent of traditional forward breeding crosses. Commercial rates of Roundup Ultra® are used during every generation of advancement, regardless of which gene deployment strategy is used to ensure that the resistance genes have been transmitted and/or the genes are present in the homozygous state.

b. Glyphosate Resistance is Conferred by a Two Recessive Genes: An adapted line (glyphosate susceptible) is cross-hybridized to a glyphosate tolerant mutant line. Resulting $F_1$ hybrid plants are not sprayed with glyphosate since the recessive genes are masked in the heterozygous state. $F_2$ seed from self-pollinated $F_1$ plants are harvested, and resulting $F_2$ plants are sprayed with 32 oz/A Roundup Ultra®. We expect the 6.25% of the $F_2$ progeny tested that are homozygous for both recessive genes to survive. All survivors are self-pollinated to produce $F_3$ seed. Resulting $F_3$ plants are screened with 32 oz/A of Roundup Ultra® to identify individuals that are homozygous for the recessive glyphosate resistance genes. All $F_3$ progeny from surviving $F_2$ plants will survive commercial application rates of glyphosate. Homozygous $F_2$ or $F_3$ plants with the recessive resistance genes are used as donor parents for introgressing the genes into adapted germplasm through backcross breeding or as a parent of traditional forward breeding crosses. After each generation of crossing, resulting hybrids are self-pollinated, and resulting progeny are screened with commercial rates of Roundup Ultra® to ensure that the recessive resistance genes are present in the homozygous state.

c. Glyphosate Resistance is Conferred by a One Dominant Gene and One Recessive Gene: An adapted line (glyphosate susceptible) is cross-hybridized to a glyphosate tolerant mutant line. Seed is planted in the greenhouse but resulting $F_1$ hybrid plants will not be sprayed with glyphosate since the recessive allele is masked in the heterozygous state. $F_2$ seed is harvested from self-pollinated $F_1$ plants. Resulting $F_2$ plants are sprayed with 32 oz/A Roundup Ultra®. We expect 18.75% (i.e. genotypes that are homozygous or heterozygous for the dominant gene and are homozygous for the recessive glyphosate resistance gene) of the $F_2$ progeny to survive. Survivors are self-pollinated to produce $F_3$ seed. Resulting $F_3$ plants are screened with 64 oz/A of Roundup Ultra®, which is twice the commercial rate. Screening with 2× the recommended application rate will permit only those genotypes with high levels of resistance to survive, which is likely to eliminate genotypes that are heterozygous for the dominant gene, which is desirable. All $F_3$ progeny from surviving $F_2$ plants that are homozygous for the dominant and recessive glyphosate resistance genes, respectively, will survive. Homozygous $F_2$ or $F_3$ plants are used as donor parents for introgressing the genes into adapted germplasm through backcross breeding or as a parent of traditional forward breeding crosses. After each generation of crossing, resulting hybrids are self-pollinated, and resulting progeny are screened with 2× commercial rates of Roundup Ultra® to ensure that the dominant and the recessive resistance genes both are present in the homozygous state.

Enhancing Genetic Resistance to Glyphosate

In order to combine unique glyphosate resistance genes into the same genotype, GT mutants are hybridized with GT-Louise, as well as each other, in the greenhouse using standard controlled cross-hybridization procedures. Our hope is that the combined effect of two or three glyphosate tolerance genes from unique mutants will provide higher tolerance levels than that provided by either single gene alone.

$F_1$ hybrids resulting from each cross that survive 32 oz/A application rates of Roundup Ultra® are self-pollinated to generate segregating F$_2$ progeny for herbicide screening. Progeny are screened with 32 oz/A Roundup Ultra®, and survivors are advanced to the next generation, followed by re-testing with 64 oz/A Roundup Ultra® to confirm resistance to commercial application rates. The cycle is repeated until homozygous tolerant lines that withstand 64 oz/A rates of Roundup Ultra® are identified. Seed of these lines are increased for evaluation in multi-location, replicated field trials to access agronomic potential, and these genotypes also are cross-hybridized with agronomically superior wheat germplasm from the region to deploy the genes into other genetic backgrounds.

Deposit Information

Glyphosate-tolerant wheat varieties described herein, including but not limited to IGT07002-0, IGT07003-No. 1-0, IGT07005-No. 1-0, IGT07006-0, IGT07011-0-0, IGT07013-0-0, IGT07022-0-0, IGT07027-0-0, IGT07028-0-0, IGT07029-0-0, IGT07030-0-0, IGT07031-0-0, IGT07064-0-0, IGT07073-0-0, IGT07074-0-0, IGT07087-0, IGT07091-0, IGT07092-0, EGT07073-0, EGT07081-0, EGT07100-0, EGT07111-0, EGT07118-0, EGT07130-0, EGT07132-0, EGT07138-0, EGT07139-0, EGT07140-0, EGT07143-0, EGT07146-0, EGT07149-0, EGT07154-0, EGT07155-0, EGT07156-0, EGT07158-0, EGT07162-0, EGT07180-0, Re-Mut 3.1 M3 Bulk, Re-Mut 3.2 M3 Bulk, Re-Mut 3.3 M3 Bulk, Re-Mut 3.4 M3 Bulk, Re-Mut 3.5 M3 Bulk, Re-Mut GTL 3.4-10, Macon M2 Bulk FR2 1-10, MaconFR1-16 M4 Bulk, Macon FR3-1 M2, TaraFR1-15-57, TaraFR1-15-94, TaraFR1-20-2, Tara 0.4.1, Tara 0.4.2, Tara 0.4.3, Tara 0.4.4, Tara 0.4.5, Tara 0.4.6, Alpowa M2 Bulk FR2 1-32, Louise M2 Bulk FR2 1-45, Louise Double Mutated M2 Bulk FR2 1-13, Louise FR3-1, Louise FR1-33-6, Louise FR1-42, Louise FR1-43, Louise FR1-62, Louise FR1-65-2, and Hollis FR1-9-14 are grown in plots at Washington State University, Pullman, Wash., 99164. Access to such plants and seeds thereof will be available during the pendency of this application to persons determined by the Commissioner of Patents and Trademarks to be entitled thereto under 37 CFR 1.14 and 35 USC 122. Upon allowance of any claims in this application, all restrictions on the availability to the public of the variety will be irrevocably removed by affording access to a deposit of at least 2,500 seeds of the same variety with the American Type Culture Collection, Manassas, Va. or other seed depository recognized under the Budapest Convention.

Wheat varieties Louise FR1-65-2 and Hollis FR1-9-14 were deposited in the American Type Culture Collection (10801 University Boulevard, Manassas, Va. 20110) on May 30, 2014, as ATCC Accession Nos. PTA-121317 and PTA-121318, respectively.

Applicant does not waive any infringement of their rights granted under this patent or under the Plant Variety Protection Act (7 U.S.C. 2321 et seq.).

References

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A wheat plant, or a part thereof, comprising a mutation that confers glyphosate tolerance, wherein the wheat plant or part thereof is Louise FR1-65-2 (ATCC No. PTA-121317), Hollis FR1-9-14 (ATCC No. PTA-121318), or F$_1$ progeny or self-progeny produced therefrom.

2. The wheat plant, or part thereof, of claim 1 wherein the wheat plant is tolerant to an application rate in the field of 0.84 kg ae/ha or more of the acid equivalent applied as an isopropylamine salt of glyphosate.

3. The wheat plant, or part thereof, of claim 1 wherein the wheat plant is tolerant to an application rate in the field of 1.68 kg ae/ha or more of the acid equivalent applied as an isopropylamine salt of glyphosate.

4. The F1 progeny of claim 1, wherein said progeny is a hybrid further comprising an additional trait selected from the group consisting of: male sterility, resistance to an herbicide other than glyphosate, insect resistance, disease resistance, waxy starch, modified fatty acid metabolism, modified phytic acid metabolism, modified carbohydrate metabolism, modified waxy starch content, modified gluten content, and modified water stress tolerance.

5. The F1 progeny of claim 4, wherein the additional trait is a disease resistance trait.

6. The F1 progeny of claim 5, wherein the disease resistance trait comprises resistance to *Rhizoctonia* root rot.

7. A true breeding seed that produces the wheat plant of claim 1.

8. A wheat plant, or part thereof, having all the physiological and morphological characteristics of the wheat plant of claim 1.

9. A method of producing a glyphosate-tolerant plant comprising:
   (a) crossing a plant of a selected wheat variety with the glyphosate-tolerant wheat plant of claim 1, thereby producing a plurality of progeny; and
   (b) selecting a progeny exhibiting a trait of glyphosate-tolerance.

10. The method of claim 9 comprising:
    (a) crossing plants grown from seed of said glyphosate-tolerant wheat plant with plants of said selected wheat variety to produce F$_1$ progeny plants;
    (b) selecting F$_1$ progeny plants that have the glyphosate-tolerance trait;
    (c) crossing the selected F$_1$ progeny plants with the plants of said selected wheat variety to produce backcross progeny plants;
    (d) selecting for backcross progeny plants that have the glyphosate-tolerance trait and physiological and morphological characteristics of said selected wheat genotype to produce selected backcross progeny plants; and
    (e) repeating steps (c) and (d) three or more times in succession to produce selected fourth or higher backcross progeny plants that comprise the glyphosate tolerance trait and all of the physiological and morphological characteristics of said selected wheat genotype as determined at the 5% significance level when grown in the same environmental conditions.

11. The method of claim 9 comprising:
    (a) crossing plants grown from seed of said glyphosate-tolerant wheat plant with plants of said selected wheat variety to produce F$_1$ progeny plants, wherein the selected wheat variety comprises an additional trait;
    (b) selecting F$_1$ progeny plants that have the additional trait to produce selected F$_1$ progeny plants;
    (c) crossing the selected progeny plants with the plants of said glyphosate-tolerant wheat genotype to produce backcross progeny plants;
    (d) selecting for backcross progeny plants that have the additional trait and physiological and morphological characteristics of said glyphosate-tolerant wheat genotype to produce selected backcross progeny plants; and (e) repeating steps (c) and (d) three or more times in succession to produce selected fourth or higher backcross progeny plants that comprise the additional trait and all of the physiological and morphological characteristics of said glyphosate-tolerant wheat genotype as determined at the 5% significance level when grown in the same environmental conditions.

12. The method of claim 11 wherein the additional trait is selected from the group consisting of male sterility, herbicide resistance, insect resistance, disease resistance and waxy starch.

13. The method of claim 12 wherein the additional trait is a disease resistance trait.

14. The method of claim 13 wherein the disease resistance trait is resistance to *Rhizoctonia* root rot.

* * * * *